United States Patent [19]

Moore et al.

[11] Patent Number: 5,459,077
[45] Date of Patent: Oct. 17, 1995

[54] METHODS FOR MODELLING TERTIARY STRUCTURES OF BIOLOGICALLY ACTIVE LIGANDS AND FOR MODELLING AGONISTS AND ANTAGONISTS THERETO

[75] Inventors: Graham J. Moore, Calgary, Canada; John M. Matsoukas, Patras, Greece

[73] Assignee: PepMetics, Inc., Calgary, Canada

[21] Appl. No.: 27,561

[22] Filed: Mar. 5, 1993

Related U.S. Application Data

[63] Continuation of Ser. No. 458,926, Dec. 29, 1989, abandoned.

[51] Int. Cl.$^6$ .................................................. G01N 24/08
[52] U.S. Cl. ...................... 436/173; 324/307; 324/312; 436/86; 436/172; 530/315; 530/316
[58] Field of Search ..................................... 324/307, 309, 324/312; 436/2, 86, 87, 172, 173, 501; 530/315, 316

[56] References Cited

U.S. PATENT DOCUMENTS

| | | | |
|---|---|---|---|
| 3,751,404 | 8/1973 | Sipos et al. | |
| 4,355,040 | 10/1982 | Furukawa et al. | 424/273 |
| 4,386,026 | 5/1983 | Ponpipom et al. | 260/112.5 R |
| 4,485,177 | 11/1984 | Siedel et al. | 436/547 |
| 4,578,361 | 3/1986 | Siedel et al. | 436/547 |
| 4,702,864 | 10/1987 | Maegolda et al. | 260/402.5 |
| 4,772,684 | 9/1988 | Brunck et al. | 530/316 |
| 4,789,832 | 12/1988 | Nagayama | 324/307 X |
| 4,818,684 | 4/1989 | Edelman et al. | 435/7 |
| 4,822,746 | 4/1989 | Walt | 436/172 X |
| 4,830,961 | 5/1989 | Petty | 436/503 |
| 4,845,075 | 7/1989 | Murray et al. | 514/12 |
| 4,849,407 | 7/1989 | Murray et al. | 514/12 |
| 4,853,871 | 8/1989 | Pantoliano et al. | 436/87 |
| 5,015,651 | 5/1991 | Carini et al. | |
| 5,043,349 | 8/1991 | Carini et al. | |

FOREIGN PATENT DOCUMENTS

| | | |
|---|---|---|
| 0253310 | 1/1988 | European Pat. Off. |
| 0323841 | 7/1989 | European Pat. Off. |
| 0324377 | 6/1990 | European Pat. Off. |
| WO90/07111 | 6/1990 | WIPO |
| 90/07110 | 6/1990 | WIPO |

OTHER PUBLICATIONS

*Chem. Abstr.* 1974, 81, Abstract No. 81:46793m.
*Chem. Abstr.* 1976, 85, Abstract No. 85:160476t.
*Chem. Abstr.* 1978, 88, Abstract No. 88:148329b.
*Chem. Abstr.* 1982, 96, Abstract No. 96:123275h.
*Chem. Abstr.* 1987, 107, Abstract No. 107:90191t.
Otter et al. "Solution Conformation of N–Acetyl–L–prolyl–glutaminyl–L–prolyl–L–prolyl–L–glutaminamide, a Pentapeptide Fragment of the Type I Collagen α–1 Chain C–Telopeptide, Determined by Phase–Sensitive Two Dimensional NMR Techniques" *J. Am. Chem. Soc.* 1987, 109, 6995–7001.
Steve Cheatham "Nuclear Magnetic Resonance Spectroscopy in Biochemistry" *J. Chem. Ed.* 1989, 66, 111–117.
Surewicz et al. "Conformational Properties of Angiotensis II in Aqueous Solution and in a Lipid Environment: A Fouvier Transform Infrared Spectroscopic Investigation" *J. Am. Chem. Soc.* 1988, 4412–4414.
Deranleau, D. A. *J. Am. Chem. Soc.* 1975, 97, 1218–1224.
Wombacher, H. et al. *Z. Naturforsh.* 1976, 31, 18–20.
Grinvald, A. et al. *Biochim. Biophys. Acta* 1976, 427, 663–678.
Mayer, R. et al. *J. Bio. Chem.* 1979, 254, 75–82.
Lown, J. W. et al. *J. Am. Chem. Soc.* 1982, 104, 3214–3216.
Tran, C. D. et al. *J. Am. Chem. Soc.* 1982, 104, 3002–3007.
Kanellis, P. et al. *Arch. Biochem. Biophys.* 1983, 220, 530–540.
Marion, D. et al. *Biochem. Biophys. Res. Commun.* 1983, 113, 967–974.
J. D. Glickson et al. *Pept. Proc. Am. Pept. Symp., 5th 1977,* 325–328.
J. P. Demonte et al. *Int. J. Pept. Protein Res.* 1981, 18, 478–486.
H. Tanaka et al. *Pept. Chem.* 1985 (Pub. 1986) 24rd, 311–316.
W. R. Laws et al. *Biochemistry* 1986, 25, 599–607.
C. O. Pabo et al. *Biochemistry* 1986, 25, 5987–5991.
M. C. Fournie–Zaluski et al. *Pept. Proc. Eur. Pepti Symp,* 19th 1986, 345–348.
G. Bovermann et al. *Pept. Proc. Eur. Pept. Symp.* 19th, 1986, 311–314.
G. V. Nikiforovich et al, *J. Biomol. Struct. Dyn.* 1987, 4, 1119–1135.
R. T. Gampe et al. *Biopolymers* 1988, 27, 313–321.
R. T. *Science* 1992, 256, 441.
J. S. Dixon *Trends Biochem.* 1992, 10, 357–363.
Moore, et al, "Angiotensin as a model for hormone—receptor interactions", *Bioscience Reports*, vol. 5 (1985), pp. 407–416.
Moore, et al, "Structure–desensitization relationships of angiotensin analogues in the rat isolated uterus", *Can. J. Physiol. Pharmacol.,* vol. 63 (1985), pp. 966–991.
Matsoukas, et al, "Proton Magnetic Resonance Studies of Angiotensin II Conformation: cis–trans Isomerism in Sarcosine$^7$–Containing Analogs", *Archives of Biochemistry and Biophysics*, vol. 248, No. 1 (1986), pp. 419–423.
Rauk, et al, "Mechanistic Consequences of Charge Transfer Systems in Serine Proteases and Angiotensin: Semiempirical Computations", *Biochemical and Biophysical Research Communications*, vol. 145, No. 3 (1987), pp. 1349–1355.
Matsoukas, et al, "NMR and Mass Spectroscopic Studies of the Competitive Angiotensin II Antagonist 'Sarmesin'", *Spectroscopy Letters*, vol. 21, No. 5 (1988), pp. 477–491.

(List continued on next page.)

*Primary Examiner*—James C. Housel
*Assistant Examiner*—Arlen Sodenquist
*Attorney, Agent, or Firm*—Burns, Doane, Swecker & Mathis

[57] ABSTRACT

Disclosed are methods for modelling the three-dimensional structure (tertiary structure) of a ligand having one or more active sites employing a charge-transfer interaction. Also disclosed is a model for Angiotensin II derived from such method.

20 Claims, 13 Drawing Sheets

OTHER PUBLICATIONS

Moore, et al, "Methods for Analyzing and Interpreting Cooperativity in Dose–Response Curves–I. Antagonist Effects on Agiotensin Receptors in Smooth Muscle", *General Pharmacology*, vol. 20, No. 2 (1989), pp. 193–198.

Moore, et al., "Angiotensin 'Antipeptides': (–)Messenger RNA Complementary to Human Angiotensin II (+)Messenger RNA Encodes an Angiotensin Receptor Antagonist", *Biochemical and Biophysical Research Communications*, vol. 160, No. 3 (1989), pp. 1387–1391.

Fisher, et al., *Biochemistry*, "1H NMR Studies of Bovine and Porcine Phospholipase A2: Assignment of Aromatic Resonances and Evidence for a Conformational Equilibrium in Solution", 28(11):5939–5946 (1989).

Moore, et al., *Biochemistry*, "$^1$H NMR Studies of Plastocyanin from *Scenedesmus obliquus*: Complete Sequence–Specific Assignment, Secondary Analysis, and Global Fold", 27:7806–7816 (1988).

Ostrovskii, et al., *Soviet Journal of Quantum Electronics*, "Investigation of the Dynamics of the Structure of Biopolymers by the Method of Kinetic Spectrofluorometry", 16:772–775 (1986).

Kaiser, et al, *Science*, "Amphiphilic Secondary Structure: Design of Peptide Hormones" 223:249–255 (1984).

*Chemical Abstracts*, vol. 100, No. 23, 4 Jun. 1984, Abstract No. 192245m.

*Chemical Abstracts*, vol. 104, No. 21, 26 May 1986, Abstract No. 182239f.

*Chemical Abstracts*, vol. 97, No. 1, 5 Jul. 1982, Abstract No. 2458g.

*Chemical Abstracts*, vol. 102, No. 23, 10 Jun. 1985, Abstract No. 204280a.

Moore, *International Journal of Peptide and Protein Research*, "Kinetices of Acetylation–Deacetylation of Angiotensin II", 26(5):469–481 (1985).

Matsoukas, et al., *J. Med. Chem.*, "Importance of the N–terminal Domain of the Type II Aniotensin Antagonist Sarmesin for Receptor Blockade", 31(7):1418–1421 (1988).

Duncia, et al., *J. Med. Chem.*, "The discovery of Potent Non–Peptide Angiotensin II Receptor Antagonists: A New Class of Potent Antihypertensives", 33(5):1312–1329 (1990).

Carini, et al., *J. Med. Chem.*, "Nonpeptide Angiotensin II Receptor Antagonists: N–[(Benzyloxy)benzyl]imida–zoles and Related Compounds as Potent Antihyper–tensives", 33:1330–1336 (1990).

Chary, et al., "Molecular Conformation of Gonadoliberin Using Two–Dimensional NMR Spectroscopy", Eur. J. Biochem., 158:323–322 (1986).

Skoog and West, "Principles of Instrumental Analysis", 2nd Edition, pp. 280–297.

Goghari, et al, "Structure–Activity Relationships for the Competitive Angiotensin Antagonist [Saricosine$^1$, O–methyltyrosine$^4$] angiotensin II (Sarmesin)", *Journal of Medicinal Chemistry*, vol. 29, No. 6 (1986), pp. 1121–1124.

Matsoukas, et al, "Synthesis and Biological Activities of Analogues of Angiotensin II and III Containing O–Methyltyrosine and D–Tryptophan", *Journal of Medicinal Chemistry*, vol. 28, No. 6 (1985), pp. 780–783.

Wong, et al, "Nonpeptide Angiotensin II Receptor Antagonists. IV. EXP6155 and EXP6803", *Hypertension*, vol. 13, No. 5 (May 1989), pp. 489–497.

Kessler, et al, "Separation of Cross–Relaxation and J Cross–Peaks in 2D Rotating–Frame NMR Spectroscopy", *Journal of American Chemical Society*, vol. 109, No. 2 (1987), pp. 607–609.

Moore, et al, "Synthesis of Angiotensin II Antagonists Containing Sarcosine in Position 7", Journal of Medicinal Chemistry, vol. 22, No. 9 (1979), pp. 1147–1149.

Scanlon, et al, "A New Approach to Angiotensin Antagonists: Methylation of the Tyrosine Hydroxyl in Angiotensin II", *Life Sciences*, vol. 34, No. 4 (1984), pp. 317–321.

Higashijima, T. et al, *Eur. J. Biochem.* 1984, 140, 163–171.

Ross, J. B. A. et al. *Biochemistry*, 1986, 25, 607–612.

Devaux, P. F. et al. *Biochem. Biophys. Acta* 1985, 822, 63–125.

Hass, E. et al. *Biochemistry*, 1987, 26, 1672–1683.

Weaver, A. J. et al. *Biochemistry*, 1989, 28, 8614–8623.

Weaver, A. J. et al. *Biochemistry* 1989, 28, 8624–8639.

*Chemical Abstracts* 1987, 107, Abstract No. 107:147522h.

*Chem. Abstr.* 1987, 107, Abstract No. 107:147524k.

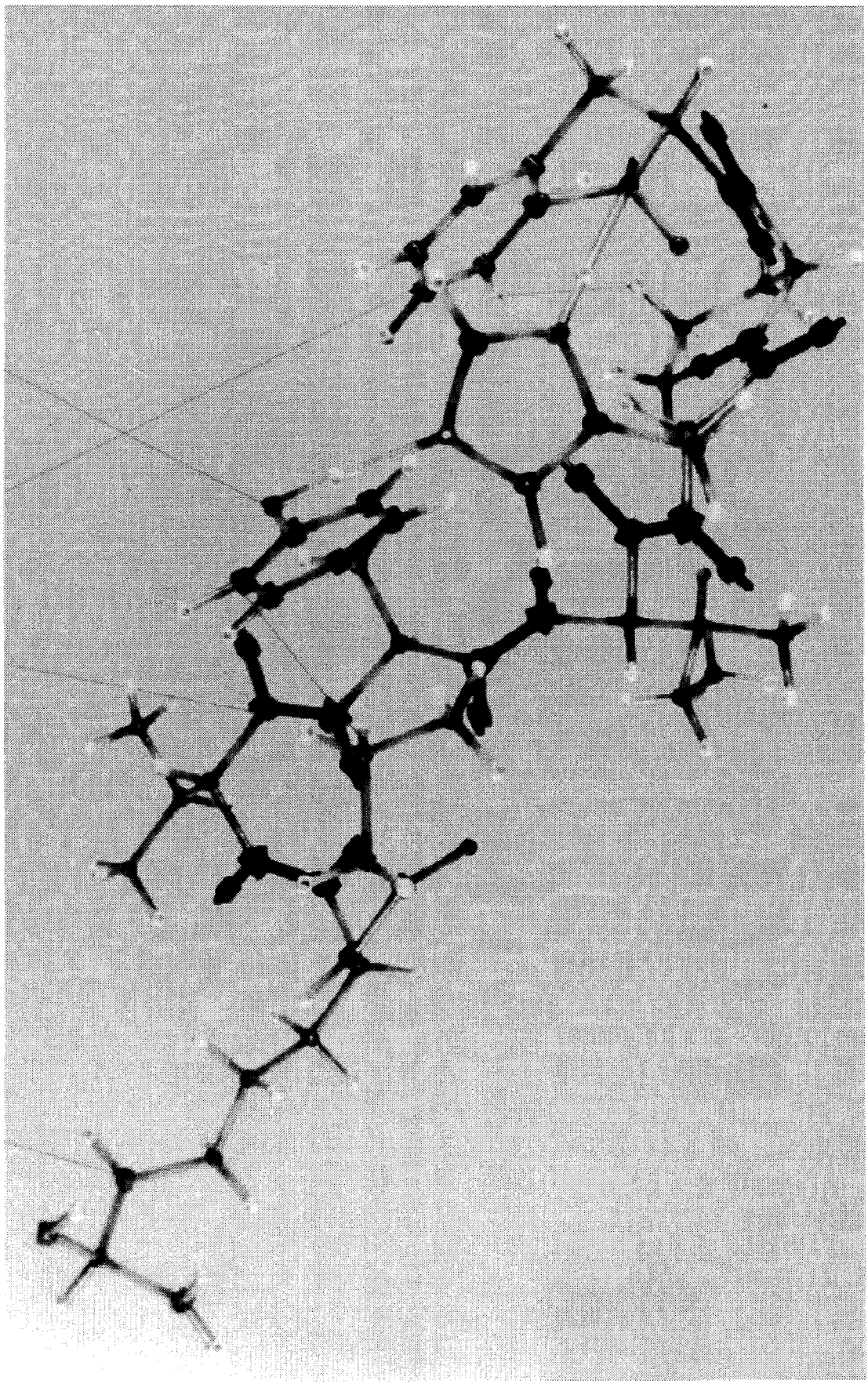
FIG._1

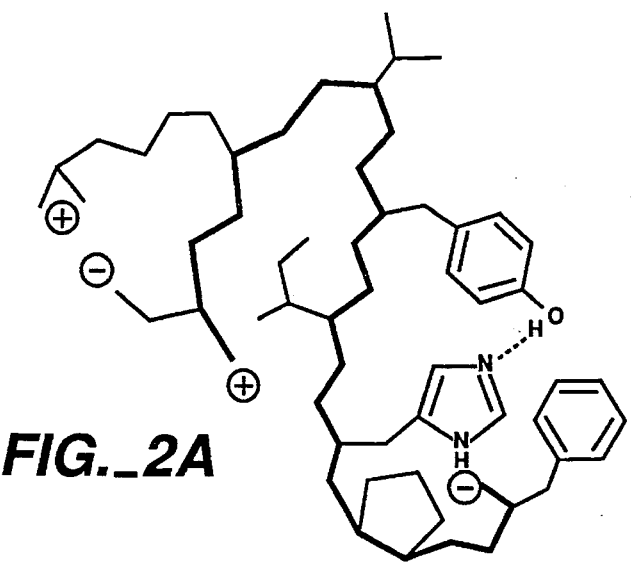
*FIG._2A*
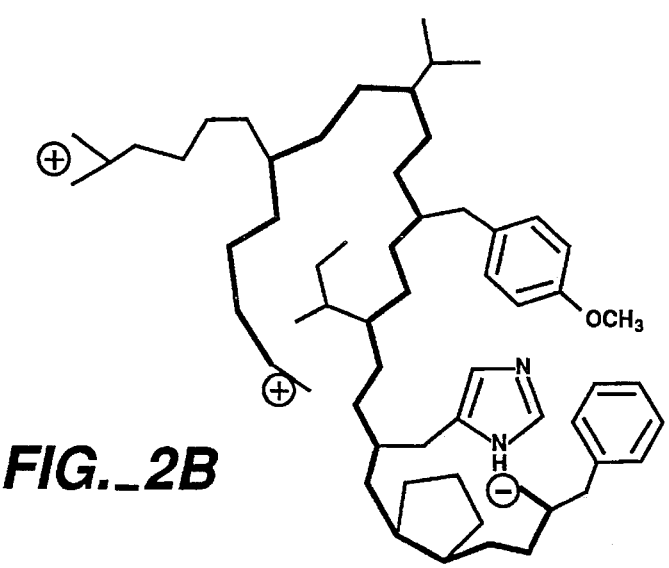
*FIG._2B*
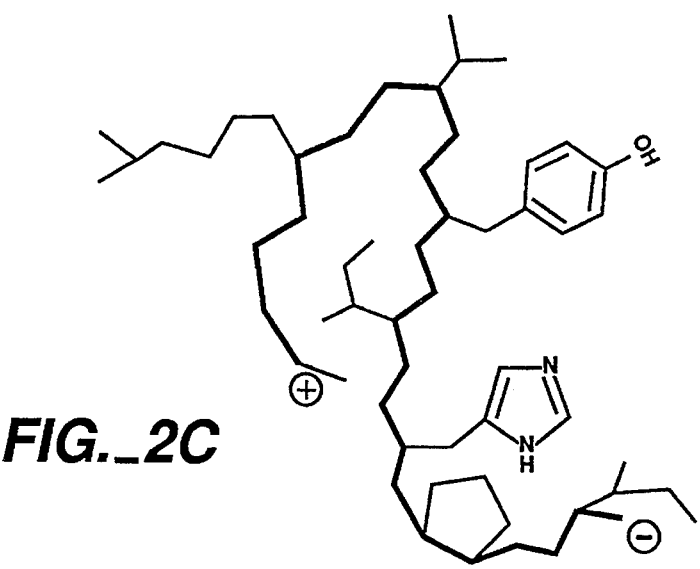
*FIG._2C*

BI
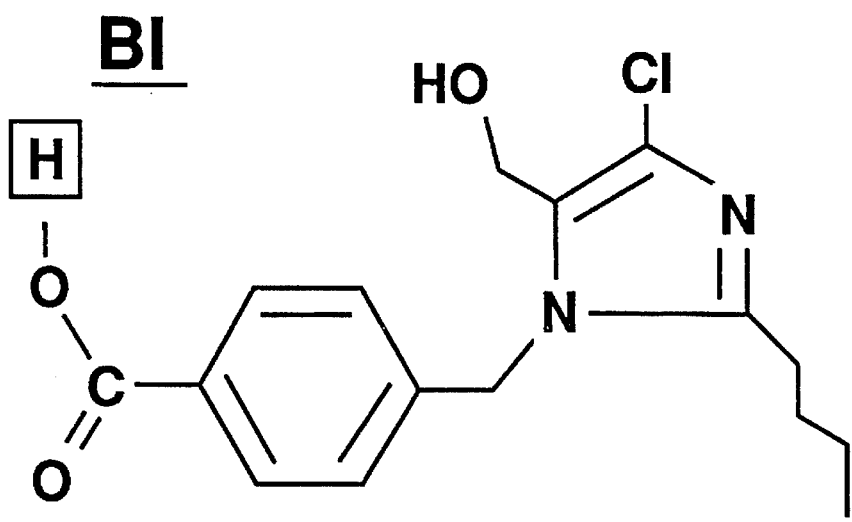
*FIG._3A*
BABI
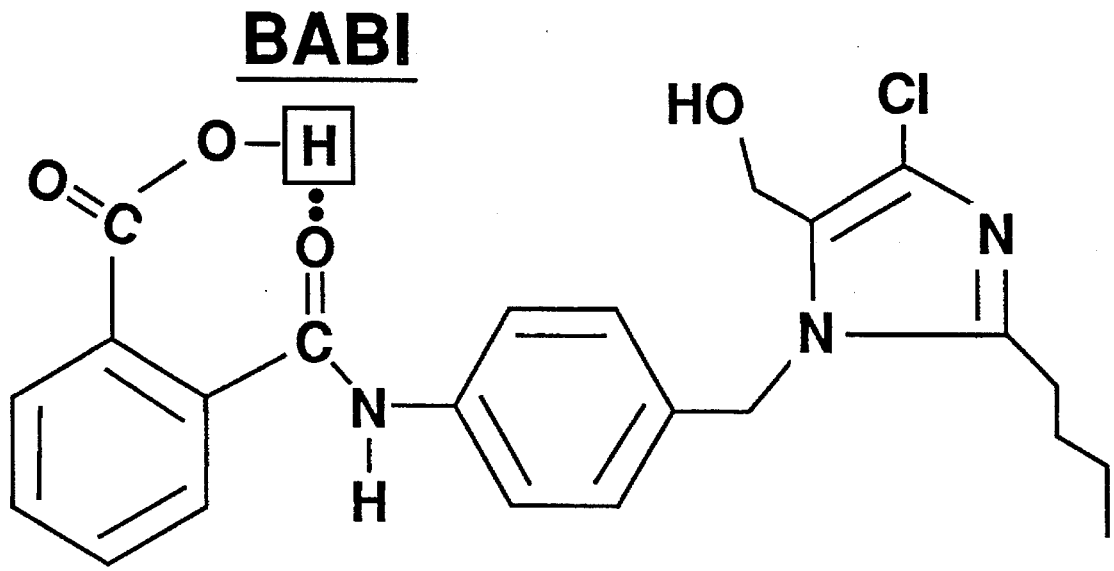
*FIG._3B*

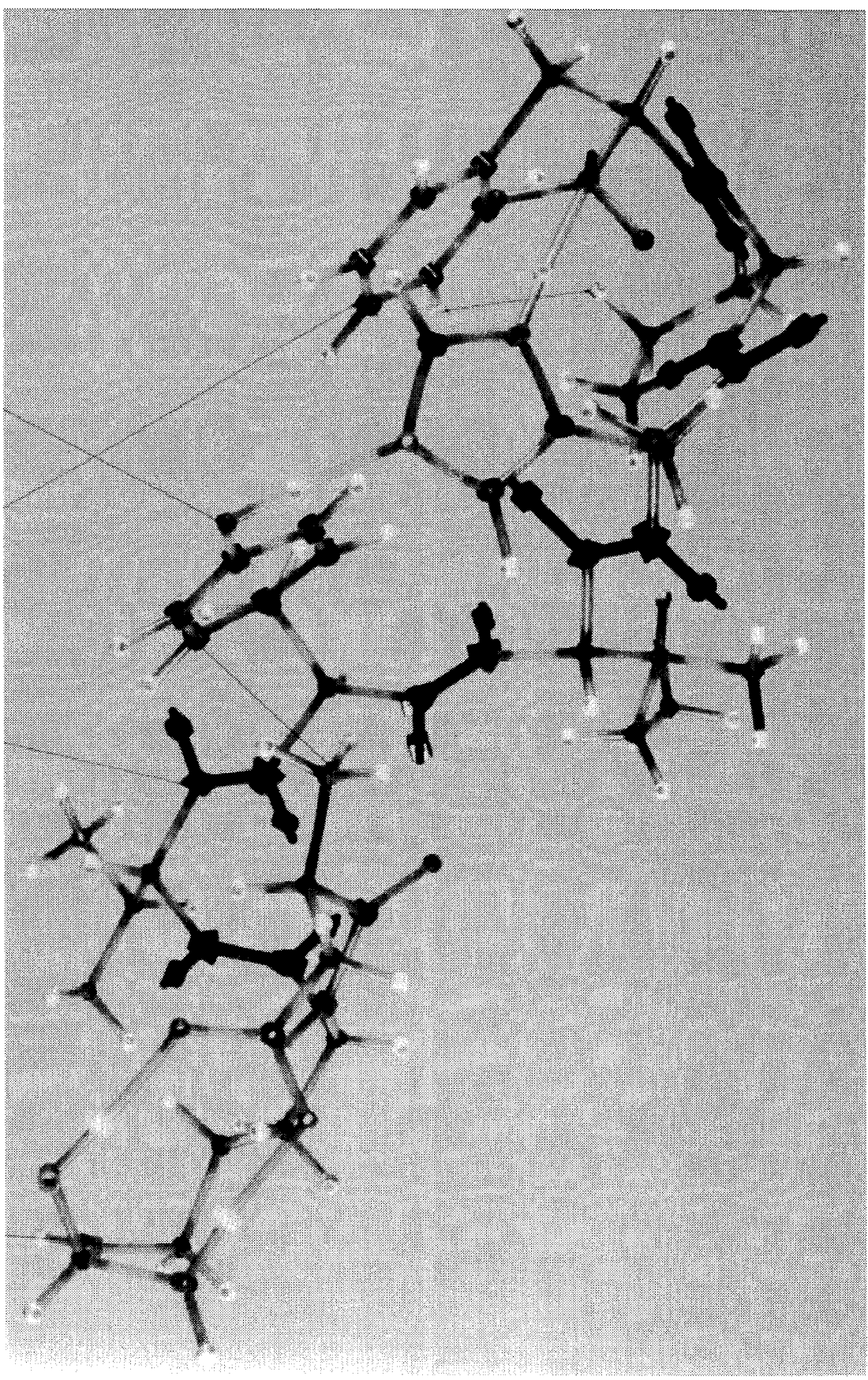
FIG._4A

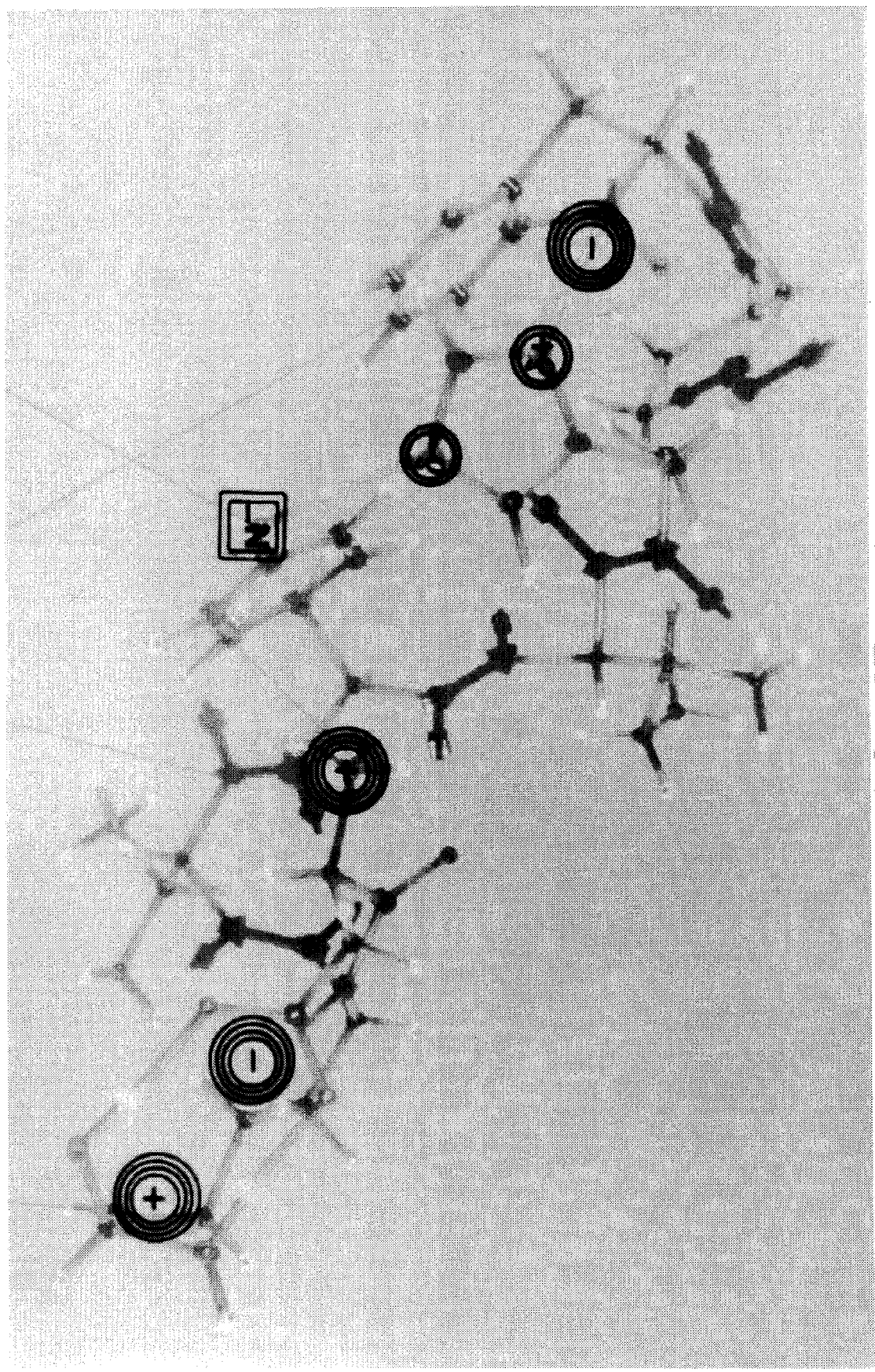
FIG._4B

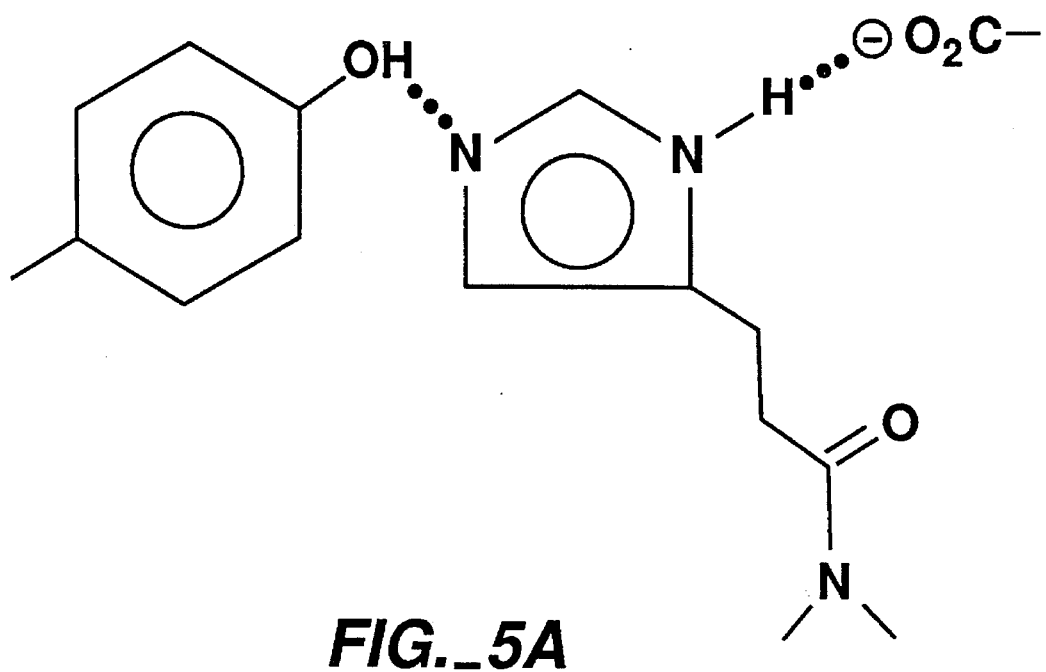
*FIG._5A*
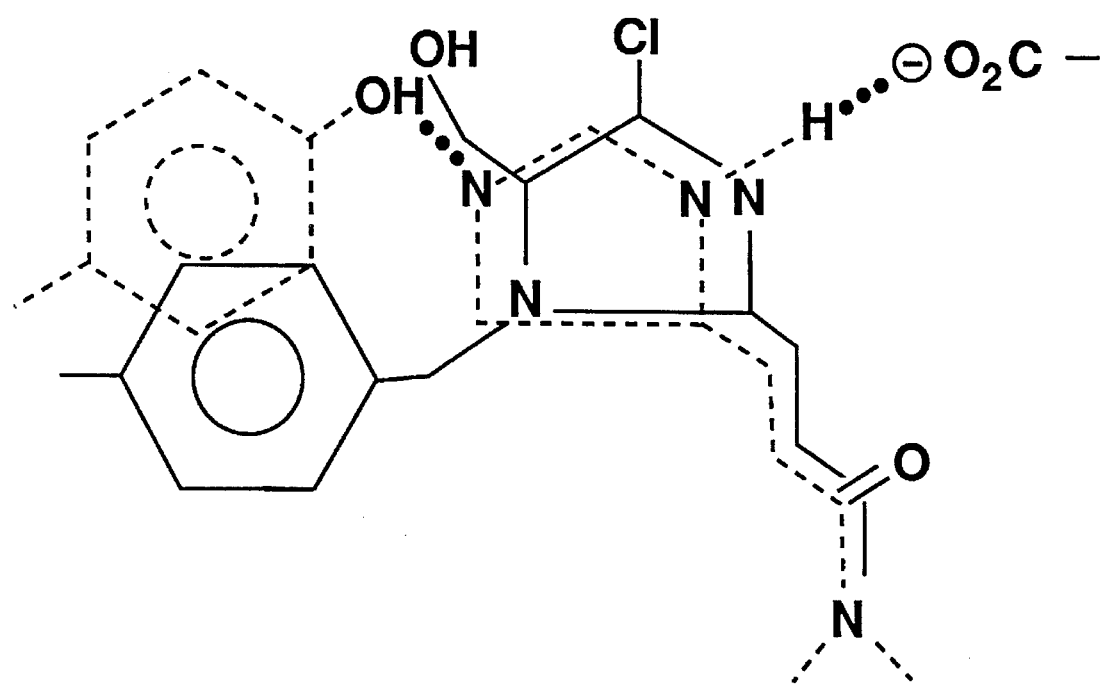
*FIG._5B*

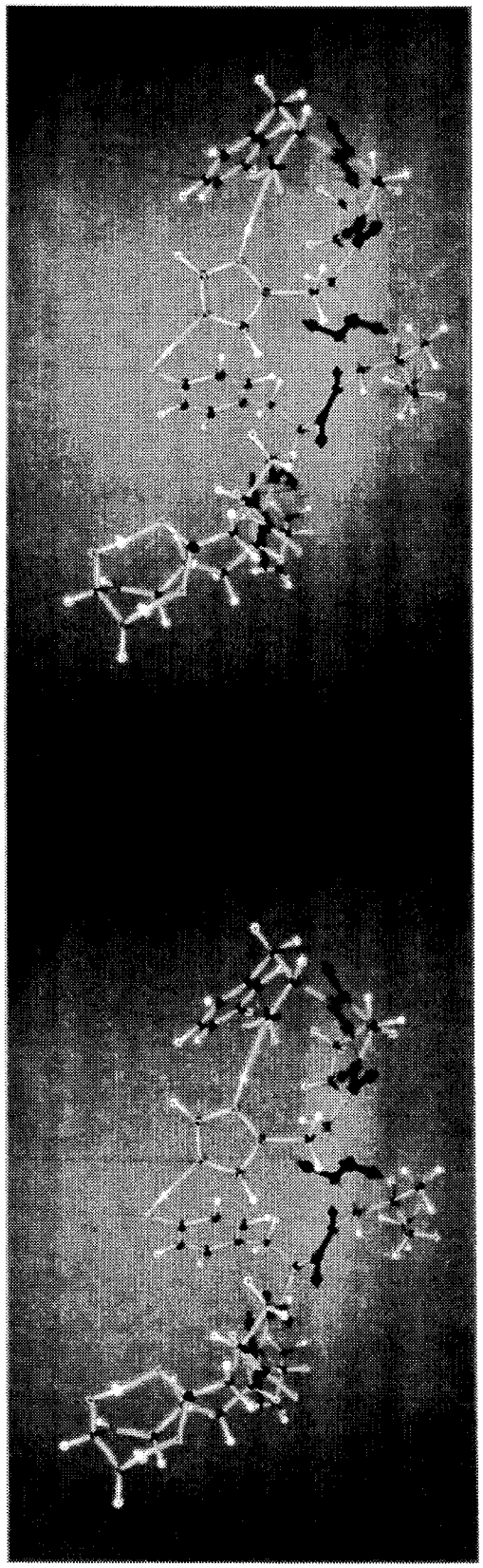
FIG._6

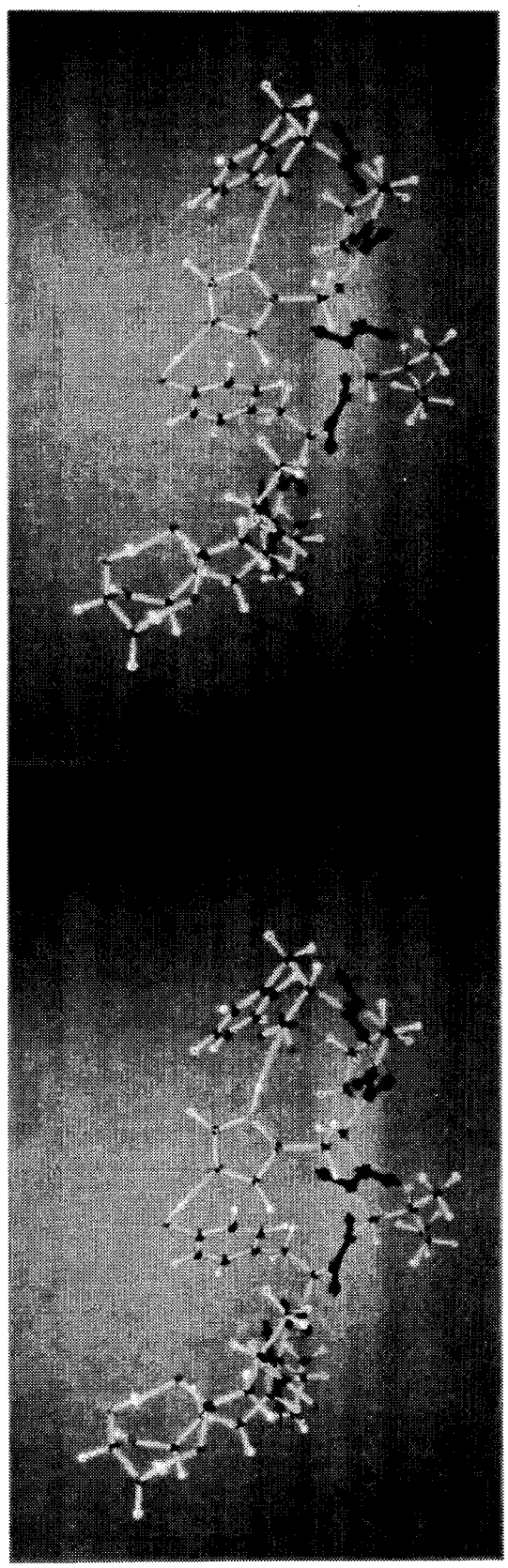
FIG._7

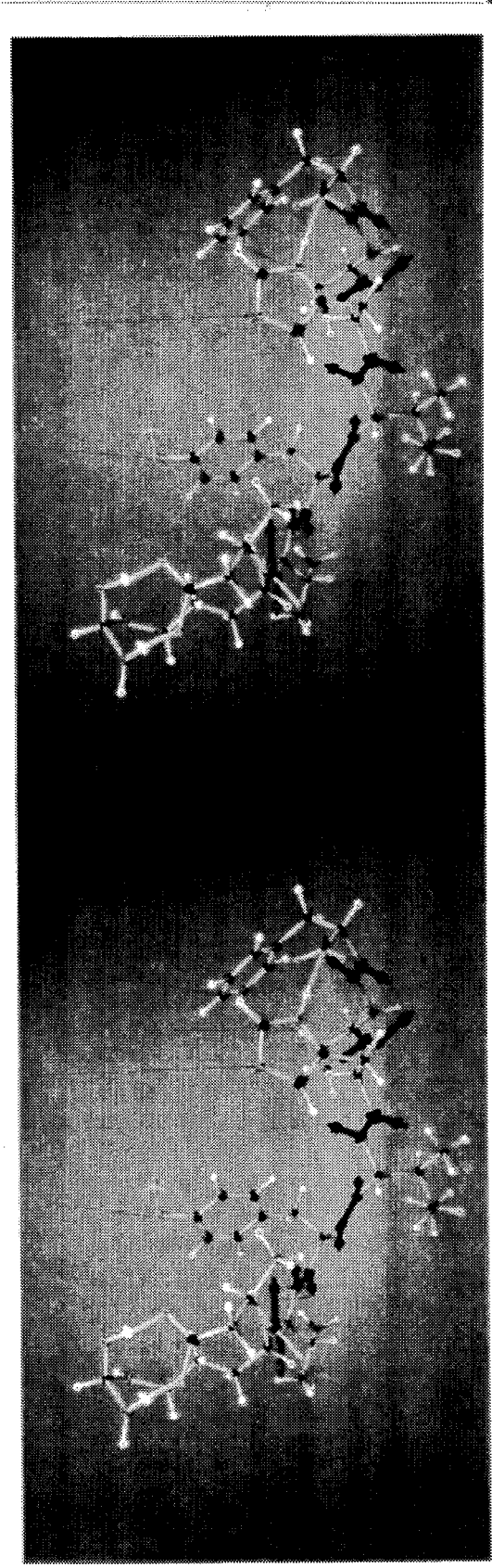
FIG._8A

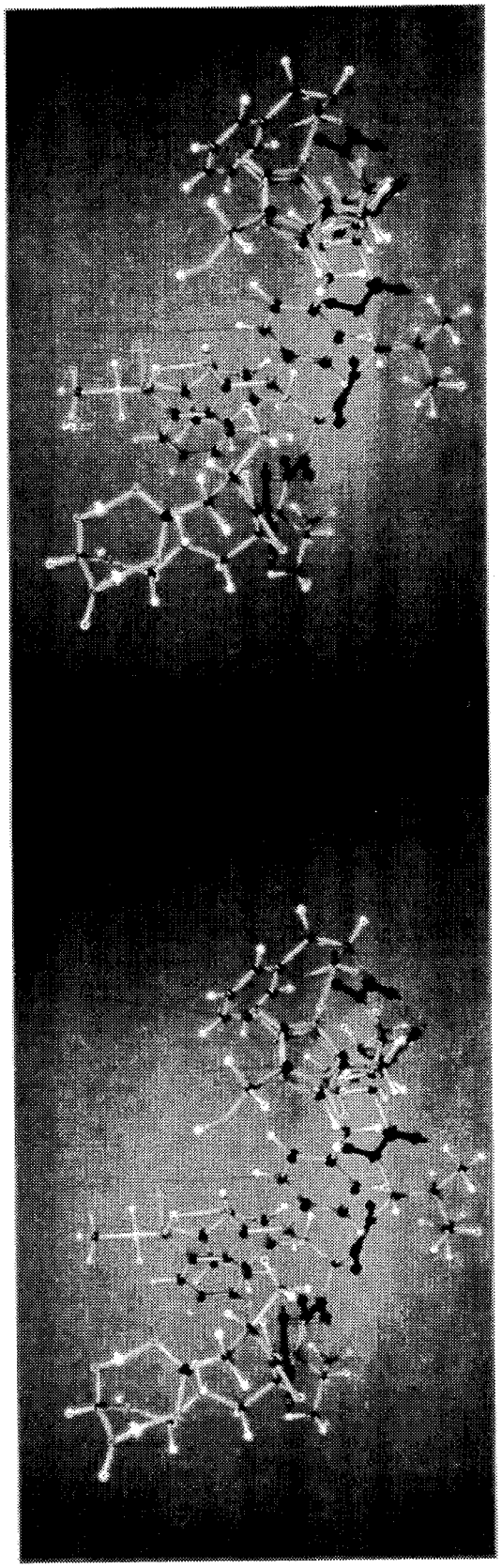
FIG._8B

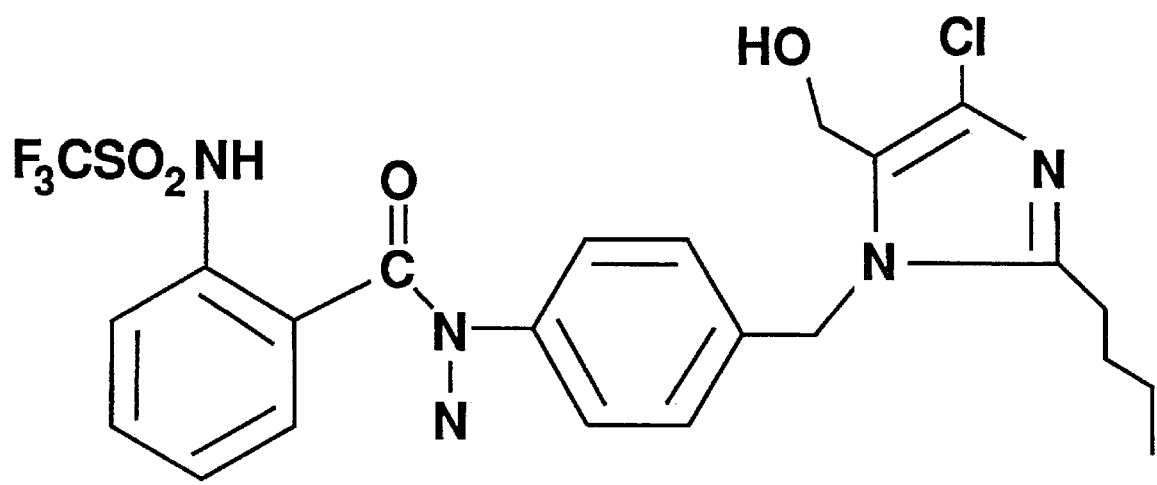
FIG._8C

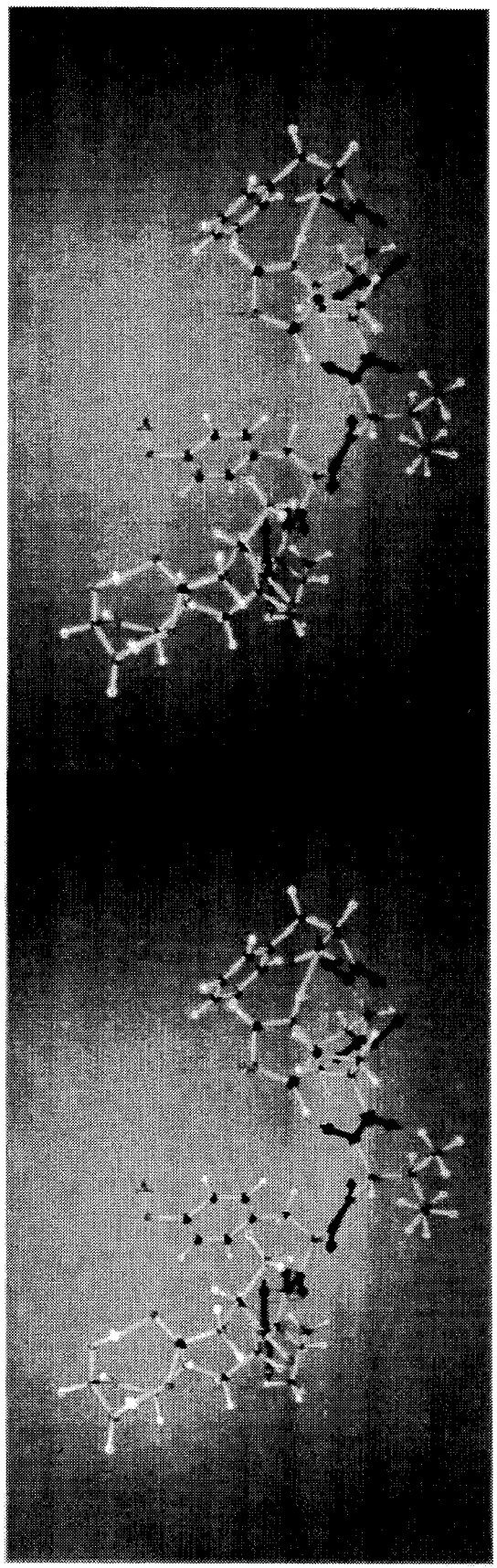
FIG.—9A

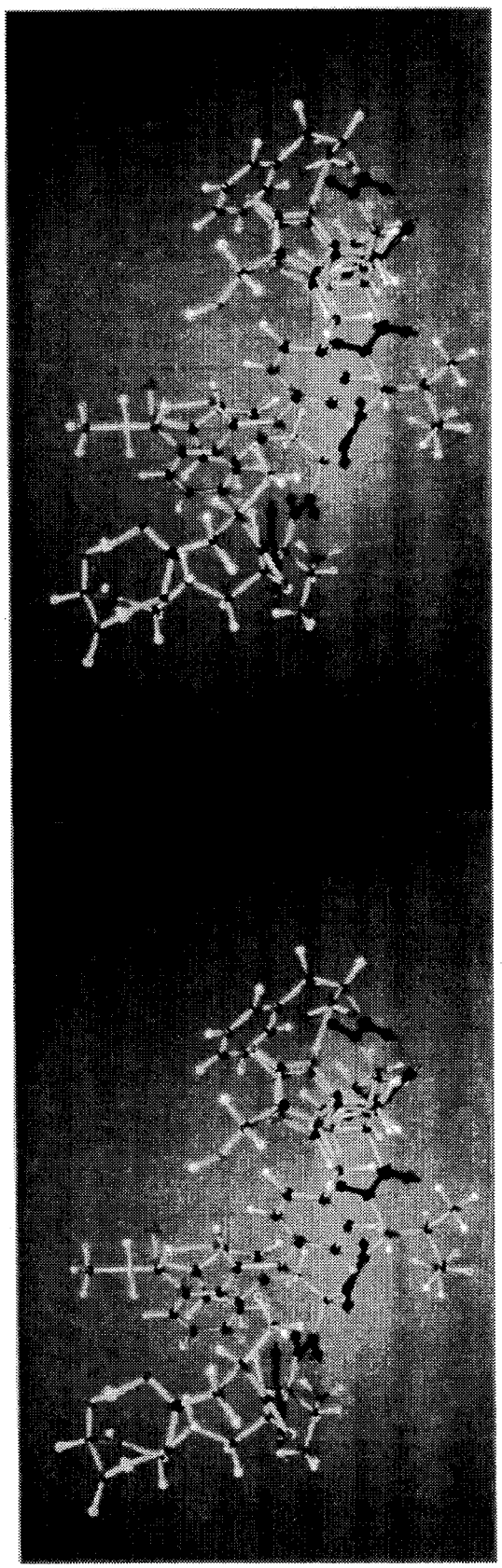
FIG._9B

METHODS FOR MODELLING TERTIARY STRUCTURES OF BIOLOGICALLY ACTIVE LIGANDS AND FOR MODELLING AGONISTS AND ANTAGONISTS THERETO

This application is a continuation of application Ser. No. 07/458,926, filed Dec. 29, 1989, now abandoned.

BACKGROUND OF THE INVENTION

1. Field of the Invention

The present invention is directed to methods for modelling tertiary (three-dimensional) structures of biologically active ligands, to methods for designing and synthesizing agonists and antagonists to the ligands based on the three-dimensional models generated for such ligands, and to the model itself generated for Angiotensin II from the methods of this invention.

2. State of the Art

In the field of chemistry, compounds can be defined in several ways. For example, a compound can be defined by its empirical formula, e.g., in the case of n-hexane the empirical formula would simply be $C_6H_{14}$. For simple molecules such as water, methane, carbon dioxide, etc., the empirical formula can provide useful information.

However, as the complexity of the molecule increases, the empirical formula must be complemented by structural information concerning the covalent bonding of the individual atoms vis-`a-vis each other in order to derive meaningful information concerning the molecule. Such information is generally depicted as a two-dimensional representation (primary structure) of the covalent bonds between the respective atoms. Such primary structures are well known pictorial representations of the compound of interest. These representations are usually defined as the structural formula of the compound which, for example, in the case of say n-hexane would be represented as:

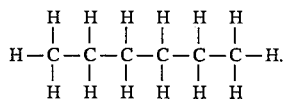

However, even with the molecule's structural formula, valuable information is still missing regarding the position in three-dimensional space of the individual atoms relative to each other. Such three-dimensional structures or conformations for a molecule are determined in part by non-covalent interactions, e.g., electrostatic and non-electrostatic interactions such as ionic interactions, hydrogen bonding, Van der Waal forces, etc., between different atoms of the molecule.

Three-dimensional information, i.e., the ligand's conformation, is extremely valuable for naturally occurring biologically active ligands. In particular, such biologically active ligands generally have one or more active sites on or within the molecular structure of the ligand. Such active sites can involve a charge-transfer interaction (as later defined). When such a ligand is bound to its complementary receptor molecule, the active site activates the receptor molecule thereby affecting the biological activity of the receptor molecule. Thus, activation of the active site, whether by a charge-transfer interaction mechanism or by some other mechanism, is generally a necessary step in affecting the biological activity of the receptor. Further in this regard, if it were possible to create an accurate three-dimensional model of the naturally occurring biologically active ligand [including its active site(s)] as found in vivo, then such models could be used to create mimetics, e.g., agonists and antagonists, of such ligands. For example, if it is desirable to suppress the biological activity of the receptor in vivo, then an accurate three-dimensional model of the receptor's naturally occurring complementary ligand including its active site(s), would greatly facilitate the preparation of antagonists to this receptor. Likewise, an accurate three-dimensional model of the ligand of interest would also facilitate the design and synthesis of agonists when it is desirable to increase or to stimulate the biological activity of the receptor in vivo.

While three-dimensional models have heretofore been proposed for molecules including ligands, such three-dimensional representations have suffered from one or more serious drawbacks, particularly as they relate to biologically active ligands having active site(s) which employ a charge-transfer interaction. In particular, such prior art methods have failed to provide a simple means to identify the active site(s) of such ligands. Accordingly, in such cases, the creation of a three-dimensional model of such a ligand including its active site was generally conducted by extremely laborious procedures such as structure-activity relationships, theoretical considerations, etc. However, because such procedures are unable to identify a charge-transfer interaction at the active site of these ligands, it has not been possible to model mimetics of such ligands to a meaningful conformation.

Additionally, other art recognized methods of modelling the tertiary structure of a compound in three-dimensional space, such as x-ray crystallography, have the drawback that with biologically active ligands, the steps required to prepare the ligand for analysis can change the ligand's tertiary structure and accordingly, the structure as determined by this analysis may not conform to the structure found in vivo. Moreover, not all biologically active ligands are amenable to such analysis.

In view of the above, it is an object of this invention to develop a process which would model the three-dimensional spatial (tertiary) structure of a biologically active ligand having one or more active sites employing a charge-transfer interaction. It is a further object of this invention that this modelling identify the chemical groups at the site(s) of charge-transfer interactions. It is still a further object of this invention to create models of such ligands closely resembling the structure of the ligand found in vivo. It is still another object of this invention to design mimetics to such ligands by reference to the model generated for the ligand. These and other objects are achieved by the present invention as evidenced by the attached summary of the invention, detailed description of the invention, examples and claims.

SUMMARY OF THE INVENTION

The above objectives are achieved by the methods of the present invention. In particular, by using these methods, one is now able to model biologically active ligands having one or more active site(s) which employ charge-transfer interactions. The methods of the present invention involve identification of a charge-transfer interaction using fluorescent methods, identification of the groups involved in the charge-transfer interaction by structure-activity studies, and application of NMR methods to resolve remaining aspects of the conformation surrounding the charge-transfer interaction. Moreover, the model or conformation so obtained is used in a method to design mimetics, i.e., agonist and antagonists, of such ligands. Accordingly, in one of its method aspects, the present invention is directed to a method for creating a three-dimensional spatial model for a biologically active ligand having one or more active sites based on a charge-transfer interaction and further having a known structural formula wherein the three-dimensional spatial assignments for each of the atoms of the ligand in the model are assigned from the steps comprising:

a) determining the presence of charge-transfer interaction(s) in said ligand from fluorescence analysis of said ligand in a fluorescence compatible environment;

b) determining the chemical groups involved in said charge-transfer interaction(s); and c) resolving remaining aspects of the ligand's three-dimensional conformation by obtaining conformational information relative to the active site(s) from nuclear magnetic resonance spectroscopy employing the nuclear Overhauser effect providing that when the nuclear Overhauser effect technique employed in this step is NOESY, then the molecular weight of said ligand is either less than about 500 or greater than about 2000.

Another method aspect of the present invention is directed to a method of modelling antagonists to a biologically active receptor based on the model generated for a biologically active ligand complementary to said receptor wherein said ligand has one or more active sites based on a charge-transfer interaction and further has a known structural formula which method comprises the steps of:

a) creating a three-dimensional spatial model for said ligand by i) determining the presence of charge-transfer interaction(s) in said ligand from fluorescence analysis of said ligand in a fluorescence compatible environment;

ii) determining the chemical groups involved in said charge-transfer interaction(s); and iii) resolving remaining aspects of the ligand's three-dimensional conformation by obtaining conformational information relative to the active site(s) from nuclear magnetic resonance spectroscopy employing the nuclear Overhauser effect providing that when the nuclear Overhauser effect technique employed in this step is NOESY, then the molecular weight of said ligand is either less than about 500 or greater than about 2000; and b) identifying a compound having a three-dimensional structure sufficiently similar to said ligand so as to be complementary to said receptor and wherein at least one of the charge-transfer interactions in said compound has been compromised.

Still another method aspect of the present invention is directed to a method of modelling agonists to a biologically active receptor based on the model generated for a biologically active ligand complementary to said receptor wherein said ligand has one or more active sites based on a charge-transfer interaction and further has a known structural formula which method comprises the steps of:

a) creating a three-dimensional spatial model for said ligand by i) determining the presence of charge-transfer interaction(s) in said ligand from fluorescence analysis of said ligand in a fluorescence compatible environment;

ii) determining the chemical groups involved in said charge-transfer interaction(s); and iii) resolving remaining aspects of the ligand's three-dimensional conformation by obtaining conformational information relative to the active site(s) from nuclear magnetic resonance spectroscopy employing the nuclear Overhauser effect providing that when the nuclear Overhauser effect technique employed in this step is NOESY, then the molecular weight of said ligand is either less than about 500 or greater than about 2000; and b) identifying a compound having a three-dimensional structure sufficiently similar to said ligand so as to be complementary to said receptor and wherein the charge-transfer interaction(s) in said compound has (have) not been compromised.

Yet another method aspect of the present invention is directed to a method for determining the presence of charge-transfer interaction(s) in the tertiary structure of a biologically active ligand complementary to a biologically active receptor which comprises conducting fluorescence analysis of said ligand in a fluorescence compatible environment.

In a preferred embodiment, the above described methods are particularly suitable for modelling a three-dimensional spatial structure of Angiotensin II. FIG. 6 of this application illustrates a stereo photograph of a molecular model (three-dimensional model) for Angiotensin-II. FIG. 8A of this application illustrates a stereo photograph of a molecular model (three-dimensional) for receptor-bound Angiotensin II. Accordingly, another aspect of this invention is directed to the model of Angiotensin-II illustrated in FIG. 6 as well as the model of receptor-bound Angiotensin II illustrated in FIG. 8A.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 illustrates a molecular model (three-dimensional spatial model) for [Sar$^1$]Angiotensin II developed by the methods of the present invention.

FIG. 2A illustrates a two-dimensional representation of the Angiotensin II antagonist, Sarmesin, i.e., [Sar$^1$Tyr(Me$^4$)] Angiotensin II.

FIG. 2B illustrates a two-dimensional representation of Angiotensin II.

FIG. 2C illustrates a two-dimensional representation of the Angiotensin II antagonist, Sarilesin, i.e., [Sar$^1$Ile$^8$]Angiotensin II.

FIG. 3A illustrates a two-dimensional representation of one example of an N-benzyl-imidazole compound and FIG. 3B illustrates a two-dimensional representation of one example of an N-benzamidobenzyl-imidazole, both compounds are in a class of compounds which are Angiotensin II antagonists.

FIGS. 4A illustrates a molecular model (e.g., a three-dimensional spatial model) for Angiotensin II developed by the methods of the present invention whereas FIG. 4B illustrates a charge distribution map for Angiotensin II obtained obtained by overlaying the relative charges found in Angiotensin II onto the model illustrated in FIG. 4A.

FIG. 5A illstrates a two-dimensional structural formula of the imidazole portion of Angiotensin II whereas FIG. 5B provides an overlay of the common portions of the compounds illustrated in FIGS. 3A and 3B and depicted by solid lines onto the imidazole portion of Angiotensin II illustrated in FIG. 5A and depicted by dashed lines.

FIG. 6 is a stereo photograph of a model of Angiotensin II produced by the methods of this invention.

FIG. 7 is the same stereo photograph illustrated in FIG. 6 but, for the sake of further clarity, is provided in color.

FIG. 8A is a stereo photograph of the receptor bound form of Angiotensin II. FIG. 8B is a stereo photograph of the overlay of the compound illustrated in FIG. 8C over the receptor bound form of Angiotensin II set forth in FIG. 8A.

FIGS. 9A and 9B are the same stereo photographs illustrated in FIGS. 8A and 8B respectively, but for the sake of further clarity, are provided in color.

DETAILED DESCRIPTION OF THE INVENTION

Although investigations on the conformation of naturally occurring biologically active ligands such as Angiotensin-II have heretofore been carried out, such investigations generally did not take into account the presence of a charge-transfer interaction in the ligand which is required for receptor activation, and therefore it has not heretofore been possible to readily model ligands as well as mimetics of such ligands to a meaningful conformation. However, by the methods of the present invention which do take into account charge-transfer interactions, it is now possible to model biologically active ligands having active site(s) which employ charge-transfer interactions to a meaningful conformation. Moreover, it is also possible to use the methods of the present invention to model mimetics of such ligands. However, prior to discussing this invention in detail, the following terms will first be defined.

"Charge-transfer interaction"—is an electrostatic interaction involving a phenol residue in which an anionic charge is transferred from a charged group to an uncharged group. In one embodiment, the phenol residue is initially uncharged, i.e., phenol, and as a result of the charge-transfer interaction, this residue accepts an anionic charge from another charged group; thus in this embodiment the phenol residue becomes a phenolate residue. In another embodiment, the phenol residue is initially charged, i.e., phenolate, and as a result of the charge-transfer interaction, this residue transfers its anionic charge to an originally uncharged group; thus in this process, the phenolate residue becomes a phenol residue.

Any phenol residue found in a biologically active ligand can be employed in the charge-transfer interaction. Suitable phenol residues include those found in the amino acid tyrosine and derivatives thereof, in steroids having a phenol group such as estradiol [estra-1,3,5(10)-triene-3,17,diol] and derivatives thereof, in catecholamines such as norepinephrine and derivatives thereof, in naphthol containing ligands and the like. The above list is not meant to be an exhaustive representation of naturally occurring components employing phenol residues but rather is presented for the purpose of illustrating that such phenol residues can be found in many different biologically active ligands.

"Active sites based on charge-transfer interactions"—refers to activation site(s) in a biologically active ligand (for activating a biologically active receptor) which is (are) based on an electrostatic interaction involving a phenol residue in which an anionic charge is transferred from a charged residue to an uncharged residue. Accordingly, in such interactions at least one of the residues is either a phenol residue or a phenolate residue. In such ligands, activation of the receptor by the ligand cannot occur without the charge-transfer interaction. Charge-transfer interactions have heretofore been suggested for ligands such as Angiotensin II. See, for instance, Moore et al., Bioscience Reports, 5, pp. 407–416 (1985), which proposed that tranfer of a negative charge from the C-terminal carboxylate residue through the imidazole residue of the histidine amino acid to the tyrosine side chain results in the formation of a phenolate species which upon interaction with the receptor activates the Angiotensin II receptor. Such charge-transfer interactions allow the ligand to modify its electrostatic character into a form which allows activation of the receptor.

The charge-transfer interaction need not be an electrostatic interaction confined solely to the ligand but also could involve a transfer of charge from either a residue on the ligand to a residue on the receptor, or from a residue on the receptor to a residue on the ligand, said transfer being a necessary precondition to activation of the receptor by the ligand. For example, the formation of the tyrosinate species on the ligand can be the result of the transfer of an anionic charge from an anionic residue on the receptor. Upon formation of the tyrosinate species, the ligand is then capable of activating the receptor.

The methods of the present invention employ techniques which permit detection of charge-transfer interactions in biologically active ligands or in biologically active ligand/ biologically active receptor complexes. These techniques employ a fluorescence analysis discussed below in a fluorescence compatible environment.

"Ligand"—any organic compound for which a receptor naturally exists or can be prepared.

"Biologically active ligand"—a molecule which binds to a biologically active receptor molecule and which directly or indirectly affects the activity of the receptor molecule. Binding of such ligands to the receptor (acceptor) molecule is accordingly a necessary precondition for initiating, terminating, altering or preventing the biological activity in the receptor molecule. Any ligand which affects the biological activity of the receptor molecule is said to be a biologically active ligand. The biologically active ligand can be a substrate, an agonist, an antagonist, an activator, an inhibitor, etc. When a ligand is able to bind to a specific receptor, the ligand and receptor pair are said to be complementary. Examples of biologically active ligands are well documented in the art. Examples of important biologically active ligands include, for example, oxytocin (wherein the presently known complementary receptors are oxytocin receptor and oxytocin-neurophysin), vasopressin (wherein the presently known complementary receptors are the $V_1$ receptor, the $V_2$ receptor, and vasopressin neurophysin), Angiotensin II (where the presently known complementary receptor is known as the Angiotensin II receptor), and the like.

The biologically active ligand can be peptidic or non-peptidic in nature. Such ligands can be indigenous to the organism where the biologically active receptor is found. When the ligand is one which is naturally occurring in that organism, then that ligand is referred to as a naturally occurring biologically active ligand. On the other hand, the biologically active ligands can be synthetic molecules which are complementary to the biologically active receptor and which affect the biological activity of the receptor. Thus any molecule which is complementary to a biologically active receptor and which affects the biological activity of the receptor, is a biologically active ligand.

When binding of the biologically active ligand to the biologically active receptor and the activation of the active site results in an alteration of the biological activity of the receptor, e.g., initiates, increases, decreases or terminates the biological activity of the receptor, the ligand is said to directly affect the activity of the receptor. On the other hand, a biologically active ligand indirectly affects the activity of the biologically active receptor when the binding of the ligand to the receptor results in an inability to activate the receptor (because the ligand possess a compromised charge-transfer interaction—as in the case of a antagonist).

Activation of the active site of the naturally occurring biologically active ligand/receptor complex is generally accomplished by some sort of chemical interaction within the ligand or between the ligand and the receptor. As noted above, when the chemical interaction involves the transfer of charge from one residue to another wherein one of the residues is either a phenol or a phenolate residue, the interaction is termed a charge-transfer interaction. Such charge-transfer interactions are believed to result in the alteration of the structure of the ligand or the ligand/receptor complex which then activates the receptor. Because such charge-transfer interactions can now be detected by the techniques employed in the present invention, it is now possible to incorporate such interactions into the model created for the naturally occurring biologically active ligand and to create agonists and antagonists to the complementary receptor.

Preferably, when analyzed by nuclear magnetic resonance spectroscopy employing the nuclear Overhauser effect (as defined below), the ligand should have a molecular weight of less than about 15,000 daltons, and more preferably, less than about 10,000 daltons, even more preferably, less than about 5,000 daltons and most preferably, less than about 3,000 daltons. However, in the fluorescence analysis of this invention, any molecular weight biologically active ligand can be employed.

"Angiotensin II"—refers to the biologically active ligand which is an octapeptide represented by the amino acid sequence of

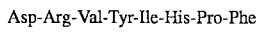
Asp-Arg-Val-Tyr-Ile-His-Pro-Phe wherein each of the above abbreviations are art recognized abbreviations for amino acids.

"Oxytocin"—refers to the biologically active ligand which is a nonapeptide represented by the amino acid sequence of

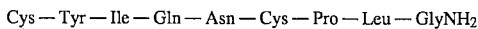
Cys — Tyr — Ile — Gln — Asn — Cys — Pro — Leu — GlyNH$_2$ wherein each of the above abbreviations are art recognized abbreviations for amino acids.

"Vasopressin" (arginine vasopressin)—refers to the biologically active ligand which is a nonapeptide represented by the amino acid sequence of

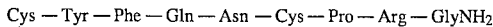
Cys — Tyr — Phe — Gln — Asn — Cys — Pro — Arg — GlyNH$_2$ wherein each of the above abbreviations are art recognized abbreviations for amino acids.

"Receptor"—a molecule which binds the ligand.

"Biologically active receptor"—a molecule, having a specific binding site for its complementary ligand, and can include classical hormone receptors, binding and/or transport proteins, enzymes, antibodies and the like. One embodiment of a biologically active receptor includes membrane bound proteins which control certain cellular processes and which themselves are regulated by the binding (or lack of binding) of its complementary naturally occurring biologically active ligand. Because such membrane bound biologically active receptors are bound to membrane, it is believed that the conformation of the biologically active ligand necessary to activate such receptors are lipid induced. See, for instance, Sargent et al., Proc. Natl. Acad. Sci. (USA), 83(16), pp. 5774–5778 (1986) and Surewicz et al., J. Amer. Chem. Soc., 110, pp. 4412–4414 (1988). On the other hand, there are other biologically active receptors which are not membrane bound. In such cases, such receptors may not require a lipid induced conformation of the biologically active ligand and, in fact, may require an aqueous induced conformation of the complementary biologically active ligand in order to activate such receptors.

Examples of biologically active receptors have been well documented in the art. Specific examples include insulin receptor (wherein the complementary ligand is insulin), the V1 receptor (wherein the complementary ligand is vasopressin), the V2 receptor (wherein the complementary ligand is vasopressin), oxytocin-neurophysin (where the complementary receptor is oxytocin), the Angiotensin II receptor (wherein the complementary ligand is Angiotensin II), and the like.

"Agonist"—A biologically active ligand which binds to its complementary biologically active receptor and activates the latter either to cause a biological response in the receptor or to enhance pre-existing biological activity of the receptor. The agonist can be the naturally occurring biologically active ligand or it can be a synthetic molecule which can also activate the receptor. For example, it is known in the art that Angiotensin II acts as an agonist for its complementary receptor, the Angiotensin II receptor. Other examples of agonists for the Angiotensin II receptor include [Sar$^1$]Angiotensin II and the like. Examples of agonists for other receptors include norepinephrine (for its complementary receptor the alpha or beta adrenergic receptors). A common characteristic of all agonists in this invention is that the charge-transfer interaction in the agonist which is necessary to activate the biologically active receptor is not compromised. That is to say that the charge-transfer interaction is operable in the agonist.

"Antagonist"—A biologically active ligand which binds to its complementary biologically active receptor and either prevents the activation of the latter or deactivates the latter so as to either prevent or diminish the biological activity of the receptor. For example, it is known in the art that the non-peptides 2-n-butyl-1-[4-carboxybenzyl]-4-chloroimidazole-5-acetic acid) and (methyl 2-n-butyl-1-[4-(2-carboxybenzamido)benzyl]-4-chloroimidazole-5-acetate, sodium salt act as antagonists of the Angiotensin II receptor. See Hypertension, 13, No. 5, May 1989. Other examples of art recognized antagonists to the Angiotensin II receptor include the peptides sarmesin, and the like. Examples of art recognized antagonists to other biologically active receptors include propranolol for the β-adrenergic receptor, cimetidine for the Histamine-H$_2$ receptor and the like. A common characteristic of all antagonists in this invention is that the charge-transfer interaction in the antagonist which is necessary to activate the biologically active receptor is compromised. That is to say that the charge-transfer interaction in the antagonist is impaired and accordingly, the antagonist cannot activate the complementary receptor. For example, one method of impairing the charge-transfer interaction is to modify the hydroxyl group from the phenol moiety by, for example, methylating, (e.g., forming the —φ—O—CH$_3$ group). Another method of impairing the charge-transfer interaction is to remove the hydroxyl group from the phenol moiety, e.g., changing phenol to phenyl.

For example and as noted above, Moore et al., Bioscience Reports, 5, pp. 407–416 (1985), proposed the presence of a charge-transfer interaction in Angiotensin II among the C-terminal carboxylate residue, the histidine amino acid and the tyrosine amino acid. In view of this charge-transfer interaction, two classes of antagonists to Angiotensin II are recognized; both of which have an impaired charge-transfer interaction. The first class involves antagonists in which the tyrosine hydroxyl group is modified or deleted and in which the N-terminal amino acid has been modified (e.g., [$Sar^1Tyr(Me)^4$]Angiotensin II, Sarmesin). The other class of antagonists to Angiotensin II involves antagonists in which the C-terminus is modified, with or without concomitant modification of other parts of the molecule (e.g., [$Sar^1Ile^8$] Angiotensin II, Sarilesin].

Thus, while an antagonist is a biologically active ligand, it is not a biologically active ligand having an active site based on a charge-transfer interaction because, by definition, this charge-transfer interaction has been impaired.

"Mimetics"—refers to agonists and antagonists to a biologically active receptor but which have a different structural formula (primary structure) than the naturally occurring biologically active ligand for said receptor. That is to say that mimetics are non-naturally occurring biologically active ligands.

"Tertiary structure of a biologically active ligand"—refers to the art recognized term which describes the three-dimensional in vivo organization of the individual atoms of such ligands including the charge distribution map so generated. The tertiary structure of a biologically active ligand (often termed its "conformation") reflects non-covalent interactions between/among atoms as well as covalent bonding between atoms. Non-covalent interactions include both electrostatic and non-electrostatic interactions such as ionic bonds, hydrogen bonding, Van der Waal forces, etc. Because the extent and nature of such non-covalent interactions are dependent on the polarity of the solvent in which they are measured, the tertiary structure (conformation) of such ligands will change when taken from its in vivo microenvironment and placed into an environment of different polarity.

"Fluorescence compatible environment"—is an environment where long lifetime fluorescence (LLF—defined hereinbelow) can be detected. In this regard, it is noted that certain solvents such as dimethylsulfoxide (DMSO) and water do not permit detection of LLF, presumably because of such factors as solvent induced fluorescence quenching, solvent interference with intramolecular hydrogen bond formation. On the other hand, the use of aqueous solutions of micelles and lipid bilayers as well as the use of solvents having a dielectric constant of about 40 or less allows for detection of LLF. Preferably, solvents having a dielectric constant of less than 40 are employed as the fluorescence compatible environment. Even more preferably, the dielectric constant fluorescence compatible environments is from about 2 to about 40. Suitable solvents having a dielectric constant of about 40 or less include, for instance, propylene glycol, isopropanol, trifluoroethanol and the like. Lastly, the solvent so selected should itself not possess fluorescence in the region where the LLF is being detected.

"Receptor-simulating environment"—refers to an environment created to simulate the polarity of the in vivo micro-environment in the immediate vicinity of a biologically active receptor. As noted above, if a biologically active ligand is placed into an environment of different polarity from its in vivo micro-environment, its tertiary structure will change but not its structural formula, i.e., the covalent bonds will not change. The addition of a biologically active ligand into a receptor-simulating environment allows the ligand to substantially conform to the tertiary structure it would possess if placed in the micro-environment of its complementary biologically active receptor. For example and as noted above, for membrane bound biologically active receptors, it is believed that the conformation of a biologically active ligand responsible for activating the receptor is lipid induced. Accordingly, for such receptors, the receptor-simulating environment will be less polar than aqueous environments and solvents having a dielectric constant of about 50 or less have been found to provide a receptor-simulating environment for such membrane bound receptors. Suitable solvents having a dielectric constant of about 50 or less include dimethylsulfoxide (DMSO), trifluoroethanol, isopropanol, propylene glycol, and the like. For non-membrane bound receptors, a solvent having a dielectric constant of about that of water or less will provide a receptor-simulating environment.

"Three-dimensional spatial model of a biologically active ligand"—refers to the tertiary structure of such a biologically active ligand created from the analytical techniques herein described. The creation of such three-dimensional spatial models is sometimes referred to herein as "modelling".

Because the NMR techniques which are employed to create the three-dimensional spatial model employ a receptor simulating environment, the model created will substantially conform to the biologically active ligand's tertiary structure. However, because the polarity of the receptor simulating environment will not be exactly the same as the in vivo micro-environment, the three-dimensional model will possess minor variations from the tertiary structure. Provided that a receptor simulating environment is employed, the resulting variations will be minor in nature and the three-dimensional spatial model will provide meaningful information concerning the in vivo tertiary structure of the biologically active ligand.

"NMR spectroscopy using the Nuclear Overhauser effect"—refers to the nuclear magnetic resonance methodology which permits insights into the three-dimensional spatial organization of the ligand's atoms. Suitable NMR methodologies include proton [$^1H$] NMR, $^{19}F$ NMR, $^{13}C$ NMR, and the like. Preferably, proton NMR is employed.

The first step of this methodology employs Correlated Spectroscopy ("COSY") which is a two-dimensional NMR spectrum yielding information on through-bond coupling patterns within a molecule. COSY methodology permits the assignment of individual proton resonances within the spectrum to particular protons in the ligand. This information is then used to identify NOE correlations. Such COSY methodology is well known in the art and is described by Cheatham, Journal of Chemical Education, 66, pp. 111–117 (1989). In some cases, COSY methodology can be supplemented by ROESY and 1-D NOE methodologies in the assignment of individual proton resonances within the spectrum to particular protons in the ligand.

Once the two-dimensional assignments have been made via the COSY methodology, the next step is to conduct nuclear magnetic resonance (NMR) employing the nuclear Overhauser effect methodology [such as one-dimensional NOE enhancement, two-dimensional NOESY and two-dimensional ROESY (rotating frame nuclear Overhauser effect spectroscopy)] on the ligand. NMR employing the nuclear Overhauser effect methodology is used to describe a change in intensity of one NMR line when another line is irradiated at the frequency of the latter line. The change in intensity is due to "through space" energy transfer from one atomic nucleus to another. Thus, the nuclear Overhauser effect provides information of nearest neighbor atomic nuclei to the line that is saturated. Accordingly, the accumulation of a sufficient number of the nuclear Overhauser effects among neighboring atoms can be used to determine the spatial characteristics for the entire molecule.

The nuclear Overhauser effect is a well known and art recognized NMR effect and is described by Cheatham, Journal of Chemical Education, 66, pp. 111–117 (1989). This reference describes the use of one-dimensional NOE enhancement as well as the use of NOE in 2-dimensional NMR (NOESY) as a tool to create three-dimensional models. The ROESY method is also well known and art recognized. The use of ROESY is particularly suitable for intermediate size molecules such as peptide hormones.

"Fluorescence analysis"—refers to the identification of a charge-transfer system in a biologically active ligand by using a fluorescence instrument capable of measuring fluorescence decay at the level of a nanosecond, or shorter, time intervals. Such equipment is known in the art and is commercially available, for example, from Photochemical Research Associates under the tradename System 3000. Fluorescence decay due to an excited-state phenolate species involved in the charge-transfer interaction is determined in a fluorescence compatible environment after excitation with light of a suitable wavelength. For example, if tyrosine is involved in the charge-transfer interaction so as to result in a tyrosinate species, fluorescence decay due to excited-state tyrosinate emitting at and around 350 nm is determined after excitation with light of a suitable wavelength, e.g., 275 nm. Other excited state species (e.g., ligands with phenol containing groups other than tyrosine) involved in the charge-transfer interaction can also be determined by measuring their fluorescence decay at a suitable wavelength after excitation at an appropriate wavelength. The appropriate wavelengths of absorption and emission can be readily determined by the skilled artisan for any given phenol containing ligand.

The experimentally obtained fluorescence decay, which is described as a sum of exponentials, is deconvoluted, and the lifetime of the longest component due to the phenolate species of interest is determined. Methods for summing the exponentials to obtain the fluorescence decay, deconvolution of the fluorscence decay and determining the lifetime of the longest component due to the phenolate species are known in the art and exemplified in the examples set forth hereinbelow.

Long lifetime fluorescence ("LLF")—is the half-life of the longest living fluorescent component emitting at or around the species' fluorescent maximum and is employed to determine the existence of a stable charge-transfer interaction occurring in the ligand. In particular, in tyrosinate excited-state fluorescence analysis in propylene glycol, LLFs greater than about 11 nanoseconds and preferably greater than about 12 nanoseconds are diagnostic that the tyrosinate moiety or modified tyrosinate moiety is participating in a stable charge-transfer interaction. Such diagnosis is made on the basis that LLF's greater than about 11 nanoseconds for tyrosine or modified tyrosine containing ligands in propylene glycol correlate to the presence of at least some (i.e., ≧1% relative to Angiotensin II) agonist activity for said ligands. On the other hand, a LLF of 11 nanoseconds or less in propylene glycol is indicative that the tyrosinate species or modified tyrosinate species responsible for the LLF is not sufficiently stable and does not activate the receptor. Again, such diagnosis is made on the basis that LLFs of about 11 nanoseconds or less for tyrosine or modified tyrosine containing ligands correlate to inactive or antagonist activity for said ligands (agonist activity of less than 1% relative to Angiotensin II). Similar correlations to determine whether a species different from tyrosine in a ligand is participating in the charge-transfer interaction can be made based on the LLFs of this species or modified species in a variety of ligands correlated to whether the particular ligand is an agonist, is an antagonist or is inactive.

Without being limited to any theory, it is believed that the charge-transfer interaction imparts a level of stability to the excited state of the species (e.g., tyrosinate), which permits a longer LLF for the species. Accordingly, longer LLFs correlate to the presence of a charge-transfer interaction which in turn correlate to agonist activity.

Having defined the terms used herein, the invention will now be described in detail.

As noted above, the first step in the preparation of a three-dimensional spatial model of a biologically active ligand having one or more charge-transfer interactions is a fluorescence analysis of the biologically active ligand. That is to say that the ligand is analyzed using fluorescence techniques in order to determine the existence of a charge-transfer interaction. In the following description of this fluorescence technique, Angiotensin II will be employed as a representative ligand. However, it is understood that other biologically active ligands can be analyzed in the same manner as Angiotensin II by using the methods hereinbelow described for Angiotensin II.

Nanosecond time-resolved fluorescence decays of Angiotensin II and analogs thereof were measured by taking advantage of the characteristic fluorescent properties of the excited-state tyrosinate species (other phenolate species would also exhibit similar characteristic properties for their excited-state). In this regard, in order for fluorescence emission from tyrosinate (and other phenolate species) to occur, there must be proton transfer to/from the phenolic hydroxyl group from/to an appropriate acceptor group. Based on the pKa's of tyrosine in the ground state (10.4) and in the excited state (less than or equal to about 5.4), protolysis in the excited-state is more efficient.

In particular, nanosecond time-resolved fluorescence decays of Angiotensin II and analogs thereof were measured from the emission at 350 nm due to its excited-state. Long lifetime fluorescence (LLF) was determined for each of these analogs in several solvents of different polarity using N-acetyl-tyrosine-amide as the reference standard. The results of this analysis demonstrate that solvents such as water and DMSO do not allow detection of long lifetime fluorescence in these analogs; presumably because of factors such as solvent induced fluorescence quenching, solvent interference with intramolecular hydrogen bond formation, etc. On the other hand, use of a fluorescence compatible environment such as aqueous lipid bilayer solutions, micelles in an aqueous environments, and solvents having a dielectric constant of about 40 or less permit the detection of long lifetime fluorescence.

Without being limited to any theory, it is believed that this detection of the long lifetime fluorescence in a fluroescence compatible environment is due to the fact that such environments either do not quench the fluorescence generated by the tyrosinate excited-state and/or do not interfere with intramolecular hydrogen bonding in Angiotensin II. Additionally, as noted above, that Angiotensin II conformation (tertiary structure) which permits the formation of a charge-transfer interaction will stabilize the tyrosinate excited-state which in turn results in very long lifetime fluorescence. Insofar as the conformation of Angiotensin II is not stagnant but in fact is dynamic (i.e., in a given environment at a given temperature, Angiotensin II is constantly changing conformation both in vitro and in vivo), only that conformation which permits formation of the charge-transfer interaction responsible for receptor activation will result in the formation of a very long lifetime fluorescence. Accordingly, the environment used for determining the presence of a charge-transfer interaction via such fluorescence analysis should be selected to be compatible with the fluorescence analysis and to allow for the presence of that conformation which permits this interaction. Such results are achieved with the fluorescence compatible environment employed in this invention. Preferably, the fluorescence compatible environment will maximize the presence of that conformation of such a biologically active ligand which actives the receptor; but such is not necessary provided that the fluorescence compatible environment permits the presence of a sufficient amount of the conformation of the biologically active ligand which activates the receptor so that its LLF can be detected.

In membrane bound receptors, recent evidence from site-specific receptor mutation studies suggests that small ligands, i.e., ligands having a molecular weight of less than about 3,000 daltons, bind to a site in one of the transmembrane domains of the receptor protein and therefore may have a biologically active conformation which is lipid-induced. In such cases, it is believed (again without being limited to such a theory) that use of solvents of intermediate polarity or less (i.e., having a dielectric constant of about 50 or less), lipid bilayers and micelles provides a receptor environment which simulates the micro-environment which the ligand encounters in the vicinity of such membrane bound receptors. Thus use of a fluorescence compatible environment for biologically active ligands complementary to such receptors provides the additional advantage that such environments should facilitate the maximization of the ligand's conformer responsible for activating the receptor.

Table I below shows the average long lifetime fluorescence values obtained from Angiotensin II and related analogs in isopropanol as well as propane-1,2-diol (propylene glycol). Table I also shows the agonist activity of Angiotensin II as well as for the listed analogs. [The data set forth in Table I below was obtained in a manner similar to that set forth in Examples 1 and 3 set forth hereinbelow].

TABLE I

| LIG- | SOLVENT | | | | AGONIST ACTIVITY[b] |
|------|---------|---|---|---|---|
| | PROPANE-1,2-DIOL | | ISOPROPANOL | | |
| AND | LLF[a] | % LLF | LLF[a] | % LLF | |
| A | 20.8 | 19 | 15.5 | 79 | 100 |
| B | 13.1 | 46 | 13.1 | 10 | 27 |
| C | 18.8 | 11 | 9.3 | 11 | 7 |
| D | 14.9 | 13 | 0 | — | 4[c] |
| E | 16.2 | 10 | 0 | — | 5[c] |
| F | 9.2 | 6 | 11.6 | 3 | 0.2 |
| G | 6.6 | 35 | 0 | — | less than 0.1 |
| H | 10.6 | 17 | 9.4 | 16 | less than 0.1 |
| I | 10.2 | 8 | 8.5 | 12 | less than 0.1 |
| J | 0 | — | 6.5 | 20 | less than 0.1[d] |
| K | 7.4 | 10 | 10.2 | 14 | 10 |

[a] = in nanoseconds
[b] = Agonist Activity was measured via a rat isolated uterus bioassay as described by Matsoukas et al., J. Med. Chem., 31, pp. 1418–1421 (1988). Results are reported relative to Angiotensin II wherein Angiotensin II = 100.

TABLE I-continued

| LIG- | SOLVENT | | | | AGONIST ACTIVITY[b] |
|------|---------|---|---|---|---|
| | PROPANE-1,2-DIOL | | ISOPROPANOL | | |
| AND | LLF[a] | % LLF | LLF[a] | % LLF | |

[c] = Potent receptor antagonist with residual agonist activity.
[d] = Potent receptor antagonist.
Ligand A = Angiotensin II
Ligand B = [Sar$^1$His(3-Me)$^6$]Angiotensin II
Ligand C = [Sar$^1$Phe$^6$]Angiotensin II
Ligand D = [Sar$^1$Cha$^8$]Angiotensin II
Ligand E = [Des$^1$Cha$^8$]Angiotensin II
Ligand F = [Sar$^1$Phe—NH$_2$8]Angiotensin II
Ligand G = [Sar$^1$Ala$^6$]Angiotensin II
Ligand H = [Sar$^1$His(1-Me)$^6$]Angiotensin II
Ligand I = [Sar$^1$D-Pro$^7$]Angiotensin II
Ligand J = [Sar$^1$Ile$^8$]Angiotensin II (Sarilesin)
Ligand K = Angiotensin III
The preparation of Ligands B–K is well known in the art. See, for instance, Matsoukas et al., Journal of Med. Chem., 31, pp. 1418–1421 (1988).
Sar = sarcosine
Cha = cyclohexylalanine
Des = amino acid residue omitted In Table I above, % LLF measures the percent of conformer(s) present which give rise to LLF.

The above data demonstrate that strong agonists, Ligands A and B, possess a long lifetime fluorescence in isopropanol of greater than 13 nanoseconds as compared to Ligands possessing either low agonist activity, antagonist activity or inactivity, Ligands C–K. Likewise, in propylene gylcol, Ligands (except Angiotensin III) possessing any agonist activity, Ligands A–E, possess a long lifetime fluorescence of greater than 11 nanoseconds, whereas Ligands either possessing no activity or antagonist activity without any residual agonist activity, Ligands F–J, possess a long lifetime fluorescence of 11 nanoseconds or less. Accordingly, prolonged duration of the long lifetime fluorescence correlates to agonist activity which in turn indicates that tyrosine's phenol residue is involved in the charge-transfer interaction responsible for receptor activation.

Contrasted with the readily conducted method of this invention which establishes that tyrosine is involved in the active state of Angiotensin II via fluorescence analysis, the prior art had previously determined that the tyrosine hydroxyl group of Angiotensin II played an important role in receptor activation either by preparing Angiotensin II analogs without tyrosine or by methylating the hydroxy group of tyrosine. It is clear that the process of the present invention is more facile and does not require the synthesis of numerous analogs of Angiotensin II. Moreover, modification of Angiotensin II by removal of amino acids etc., can in fact change the tertiary structure of the analog relative to Angiotensin II such that meaningful conclusions may be difficult to reach.

Once a charge-transfer interaction has been identified in the ligand via the fluorescence analysis of this invention, the next step in the process of preparing a three-dimensional spatial model of a biologically active ligand having one or more charge-transfer interactions is a determination of the chemical groups involved in the charge-transfer interaction. Such a determination can be conducted by using art recognized structure activity relationships. In this regard, these determinations are greatly facilitated by the knowledge that a phenol/phenolate species is involved in the charge-transfer interaction. Accordingly, in those ligands having only one such species (e.g., tyrosine) it is readily apparent that such a species is involved in the charge-transfer interaction.

In general, structure activity relationships are conducted by creating analogs of the ligand of interest by selectively replacing or modifying one of the components of the ligand (e.g., in the case of a peptide, an amino acid), and then determining the LLFs of the analogs. Reduction in the LLF of an analog as compared to the ligand is significant evidence that the component originally found in the ligand and subsequently replaced or modified in the analog plays a role in the charge-transfer interaction. See Ligands F and G in Table I which identify the histidine and C-terminal carboxylate in the charge-transfer interaction in Angiotensin II. Additionally, loss of agonist activity in the analog provides corroborating evidence that the component plays a role in the charge-transfer interaction. In this regard, if the ligand contains two or more phenol/phenolate species, determination which of such species are involved in the charge-transfer interaction can be made by creating analogs in which one of the two or more phenolic groups has been compromised, by for example, methylating the hydroxy group. Analysis of the LLFs and biological activities of such analogs will provide the required information to determine which of the two or more phenolic groups is involved in the charge-transfer interaction.

Once the groups involved in the charge-transfer interaction have been identified, the next step in the process of preparing a three-dimensional spatial model of a biologically active ligand having one or more charge-transfer interactions is to resolve remaining aspects of the ligand's three-dimensional spatial conformation by obtaining conformational information relative to the active site from nuclear magnetic resonance spectroscopy employing the nuclear Overhauser effect.

As noted above, this step first involves the use of COSY methodology which provides information on through-bond coupling patterns within a molecule and allows for the two-dimensional assignment of individual protons in the ligand. The COSY methodology is established in the art. After the two-dimensional assignment of the individual protons via COSY methodology, the ligand is then examined by conducting nuclear magnetic resonance employing the nuclear Overhauser effect methodology. Suitable nuclear Overhauser effect methodologies include one-dimensional NOE enhancement, two-dimensional NOESY and two-dimensional ROESY. All of these nuclear Overhauser effect methodologies are established in the art.

However, with regard to ligands having a molecular weight of between about 500 to 2000 daltons, the use of NOESY methodology often fails for such ligands, irrespective of the internuclear distances involved, because the tumbling rate for these solutes is close to that at which the maximum possible NOE passes through zero. See Bax and Davis, J. Magn. Reson., 63, pp. 207–213 (1985). Consequently, sequential assignments and the observation of interproton distances revealing structures are impossible using NOESY for such ligands. However, such ligands can be structurally analyzed using either one-dimensional NOE enhancement or ROESY methodologies.

In further regard to nuclear magnetic resonance spectroscopy using the nuclear Overhauser effect, there is a practical limit on the molecular weight of the ligand being analyzed. In particular, ligands having a molecular weight of about 15,000 daltons or greater impose to much complexity on current NOESY/ROESY methodologies to permit their use. However, in certain circumstances, one-dimensional NOE methodologies could be used. Accordingly, in this invention, ligands being investigated by nuclear magnetic resonance spectroscopy employing the nuclear Overhauser effect preferably have a molecular weight of less than about 15,000 daltons and preferably have a molecular weight of less than about 10,000 daltons.

The solvents used when conducting proton nuclear magnetic resonance spectroscopy employing the nuclear Overhauser effect are selected so as to provide a receptor simulating environment. Thus, if the biologically active receptor is a membrane bound receptor, current hypotheses suggest the role of lipid-induced peptide folding in peptide hormone-receptor interactions. See Sargent et al., Proc. Natl. Acad. Sci. (USA), 83(16), pp. 5774–5778 (1986); and Surewicz et al., J. Amer. Chem. Soc., 110, 4412–4414 (1988). Such lipid-induced peptides are generally believed to have a molecular weight of less than about 3,000 daltons. Thus, in these circumstances, the use of solvents having a dielectric constant of about 50 or less is justified. Furthermore, such dielectic constants allow for a more ordered peptide structure.

A particularly preferred solvent for use in nuclear magnetic resonance spectroscopy employing the nuclear Overhauser effect for ligands whose complementary receptor is a membrane bound receptor is dimethylsulfoxide (DMSO). In particular, DMSO is preferred because it offers several advantages over other possible solvents having a dielectric constant of about 50 or less for the following reasons: 1) the solvent allows for the buildup of NOEs to a level of detectability which is not possible in solvents such as deuterated water; 2) for the reasons noted above, the bulk dielectric environment provided by DMSO is such that it represents an environment not unlike that encountered by such peptides at their receptors, and which gives useful and practical information; 3) the spectra are characterized by sharp and well resolved proton signals which can be individually assigned using COSY methodology and are often superior to spectra obtained in solvents such as trifluoroethanol, propylene glycol and isopropanol which give broader and often overlapping signals; 4) DMSO is superior to aqueous environments for charged molecules because fewer conformations are usually sampled and conformational averaging is altered in DMSO as compared to water; and 5) the dielectric constant of DMSO (~45) is sufficiently close to the maximum dielectric constant employed in the fluorescence analysis so that minimal conformational changes are expected in the two enviroments.

When the receptor simulating environment is aqueous in nature, the use of water or a solvent mixture containing water is justified.

In any event, when the NMR methodologies described hereinabove are proton [$^1$H] NMR methodologies, deuterated solvents will be required, i.e., $d_6$-DMSO, $D_2O$ and the like.

Examples 4–6 hereinbelow set forth biologically active ligands which have been analyzed by nuclear magnetic resonance spectroscopy employing the nuclear Overhauser effect. In this regard, Examples 1–3 had already established that the tertiary structures for naturally occurring biologically active ligands (i.e., [Sar$^1$]Angiotensin II and oxytocin) employ a charge-transfer interaction to activate the biologically active receptor and which groups were involved in the charge-transfer interaction.

Further in this regard and by using the methods of the present invention, molecular models of biologically active ligands have been developed. In particular, FIG. 1 illustrates a molecular model of [Sar$^1$]Angiotensin II. In FIG. 1, the backbone of [Sar$^1$]Angiotensin II is maintained by two gamma turns maintained in part by hydrogen bonds between the Arg CO and Tyr NH and between His CO and Phe NH (not shown). [All of the molecular models depicted herein were developed using Minit Molecular Models, Cochranes, Oxford, U.K. A person skilled in the art can readily reproduce such models.]

For comparison purposes, FIGS. 2A, 2B and 2C illustrate simplified two-dimensional structures showing some conformational aspects of Sarmesin, Angiotensin II and Sarilesin, respectively. In reality, the aromatic rings lie above the peptide backbone. See FIGS. 1 and 4A.

FIG. 4A illustrates a molecular model of Angiotensin II determined in $DMSO/D_2O$ by 2D-ROESY proton NMR in a manner similar to that of Example 4. The backbone of Angiotensin II is characterized by two gamma turns maintained in part by hydrogen bonds between the Arg CO and Tyr NH and between His CO and Phe NH (not shown). FIGS. 6 and 7 illustrate three-dimensional stereo photographs of the model of Angiotensin II. In regard to the figures containing stereo photographs, is is noted that such photographs should be viewed by stereo glasses/viewer in order to obtain the three-dimensional effect. Moreover, the eyepieces of the viewer should be set at 75 mm apart. Such stereo glasses/viewers are commercially available; one source being Marivac, 1872 Garden St. Halifax, Nova Scotia, B3M 3RL, Canada.

Once a three-dimensional spatial model for a biologically active ligand has been developed using the techniques of this invention, further refinement of this model or development of even new models can be accomplished using theoretical considerations. For example, with knowledge of the three-dimensional model for Angiotensin II depicted in FIG. 4A and illustrated in the stereo photographs of FIGS. 6 and 7, it is possible by employing theoretical consideratins to create a three-dimensional model for Angiotensin II bound to its receptor, the Angiotensin II receptor. In particular, such theoretical considerations generally relate to readily available chemical pathways. For instance, because of the charge-transfer interaction, the tyrosine hydroxyl group in Angiotensin II has been converted to its tyrosinate species. The tyrosinate species, which is a strong nucleophile, can then be derivatized by the receptor resulting in transient bonding between the ligand and the receptor. Upon such bonding, tyrosine moves away from the histidine side chain because the histidine is no longer able to form a hydrogen bond with the tyrosine hydroxyl group. Moreover, slight repositioning of the histidine is also expected. Such theoretical considerations have already been forwarded. See, for instance, Moore et al., Int. J. Pept. Prot. Res., 26, pp. 469–481, (1985). In view of the above, a receptor bound three-dimensional spatial model of Angiotensin II was developed which accounts for such conformational changes which would occur if Angiotensin II behaves in the suggested manner. A stereo photograph of this model is depicted in FIG. 8A.

The validity of the resulting model can be readily verified by overlaying known antagonists onto the receptor bound model and ascertaining whether the antagonists can conform to the model. That is to say that if the model is correct, then the antagonists should be able to adapt a conformation similar to the model of the ligand so as to bind to the receptor and thereby account for their antagonist behavior. In this regard, FIGS. 3A and 3B illustrate examples of compounds from a class (i.e., structurally related compounds) of antagonists of Angiotensin II. This class is generically known as either N-benzyl-imidazole compounds ("BI") or N-benzamidobenzyl-imidazole compounds ("BABI"). It is noted that in FIG. 3B, the acidic proton in BABI is present in a hydrogen bonded form (depicted by the box around this proton together with the dots to the amido carbonyl group) somewhat analogous to the hydrogen bonded form of the tyrosinate species of Angiotensin II. Many acidic groups can exist in similar hydrogen-bonded stabilized forms in BABI compounds, e.g., carboxylate (shown), sulfate, trifluoromethylsulfonamido, and the like. It is also noted that for the BI class of compounds, the acidic proton can occupy a similar position in space to the acidic proton shown in BABI, but that the former is not stabilized by hydrogen bonding.

In FIG. 5B, the common portion of these antagonists have been overlayed onto the imidazole portion of Angiotensin II depicted in FIG. 5A which additionally shows the relative position of the components responsible for the charge-transfer interaction in Angiotensin II (note—the imidazole double bonds have been removed from FIG. 5B for the sake of clarity). In FIG. 5B, the fact that the hydroxyl group of the hydroxymethyl in both antagonists is similarly located to the tyrosine hydroxy group in Angiotensin II; the fact that the n-butyl side chain of both antagonists mimics precisely the His $C_\beta$-His $C_\alpha$-His CO-Pro N chain of Angiotensin II; and the fact that the chlorine atom in these antagonists can serve to decrease the basicity of the imidazole nucleus of these compounds, indicates that the antagonist can form a conformation with similar electronic and three-dimensional characteristics as the conformation of Angiotensin II required for generation of the charge-transfer interaction responsible for activating the receptor. However, because these antagonists lack the necessary functionality to generate the charge-transfer interaction present in Angiotensin II, they cannot activate the receptor which accordingly explains their antagonist properties.

Having generated a model for the tertiary structure of a biologically active ligand, it is now possible to design and synthesize mimetics to this ligand. For example, it is now possible to design and synthesize compounds which are sufficiently similar to the model generated for the tertiary structure of the biologically active ligand so as to be complementary to the ligand's receptor. In this regard, antagonists are created when the compound so designed and synthesized has a compromised charge-transfer interaction whereas agonists are created when the compound so designed and synthesized has an operable charge-transfer interaction, i.e., the charge-transfer interaction is not impaired. With knowledge of the model generated for the tertiary structure of a biologically active ligand, the design and synthesis of agonists and/or antagonists to the ligand's complementary receptor is well within the ability of the skilled artisan.

The present invention also offers a particular advantage in the design and synthesis of new mimetics optionally based on the structure of known mimetics coupled with knowledge of the model generated for the tertiary structure of a biologically active ligand. This particular advantage is especially applicable to designing new mimetics of Angiotensin II, which may or may not be based on the structure of known mimetics.

In particular, structure-activity relationships show that the binding affinity between Angiotensin II and its complementary receptor derives largely from Coulombic [ionic] forces originating from complementary charges between Angiotensin II and its receptor. The ionic charges on Angiotensin II are illustrated in FIG. 4B which is based on the model for Angiotensin II depicted in FIG. 4A. In FIG. 4B, $N^-$ denotes tyrosinate which relocates upon interaction with the receptor (this is shown in FIG. 8A which is a stereo photograph of receptor bound Angiotensin II). On the other hand, the N-benzyl-imidazole (BI) and N-benzamidobenzyl-imidazole (BABI) class of known antagonists to Angiotensin II [Wong et al., Hypertension, 13, pp. 489 et seq., (1989)] are devoid of many of the charges which cause Angiotensin II to bind tightly to its receptor. Overlay of the imidazole group of the BI and BABI compounds depicted in FIGS. 3A and 3B onto the imidazole group of the model for Angiotensin II depicted in FIG. 5A is illustrated in FIG. 5B. The three-dimensional organization of the chemical groups of BI and BABI compounds is such that these compounds can mimic 1) Angiotensin II, 2) Sarmesin, or 3) Sarilesin. (For example, when the imidazole-based hydroxyl group of BABI compounds is methylated, the resulting oxymethyl group occupies a similar position in space to the oxymethyl group of Sarmesin.) Overlay of a specific BABI compound (depicted in FIG. 8C) onto the receptor bound model of Angiotensin II (depicted in FIG. 8A and in color in FIG. 9A) is illustrated in the stereo photograph of FIG. 8B. As can be seen from FIG. 8B (and in color in FIG. 9B), because the BABI compound has a similar spatial arrangement to the Tyr-Val-His sequence of Angiotensin II (as well as to Sarilesin), the BABI compounds can mimic this portion of the model of Angiotensin II (and Sarilesin) so as to be complementary to the Angiotensin II receptor. Further in this regard and without being limited to any theory, it is believed that the receptor may transiently acylate, or the like, the tyrosine hydroxyl group of receptor bound Angiotensin II and alter the location of the tyrosine side-chain relative to its position in the "charge-transfer interaction" form of Angiotensin II. Moreover, it is further believed that the acidic portion of BABI compounds which is stabilized in a predisposed or "preactivated" form by a hydrogen bonding interaction with the carbonyl oxygen of the amido group (See FIG. 3B), occupies a position in space which is similar to that of the tyrosine hydroxyl group in the receptor bound model for Angiotensin II depicted in FIG. 8A. It is still further believed that a bond, similar to that formed between the "preactivated" tyrosinate group of Angiotensin II and a receptor-based acceptor group, will also be formed between the "preactivated" acid group of BABI compounds and the receptor. In contrast to Angiotensin II, it is also believed that for the case of BABI compounds, this will not result in receptor activation because of the different conformational constraints and the nature of the ligand-receptor bond. Thus, for example, if the receptor acylates the tyrosine OH group of Angiotensin II, the adduct formed between Angiotensin II and its receptor will involve an ester bond, whereas that for the BABI compound shown in FIG. 3B will involve an anhydride linkage or for the BABI compound shown in FIG. 8C will involve an amide linkage. This discloses the fact that BABI compounds are Angiotensin II receptor antagonists because they can act as transition state inhibitors or suicide substrates for the Angiotensin II receptor. In contrast to BABI compounds, BI compounds are not likely to act by this mechanism because the acidic proton is not stabilized by hydrogen bonding, and is therefore not preactivated.

In any event, it is seen that the BI/BABI class of compounds commonly possess an imidazole ring which can be modified to enhance the potency of these compounds.

This information, in conjunction with the charge distribution map depicted in FIG. 4B, allows for the design and synthesis of new antagonists to the Angiotensin II receptor based on incorporating additional charges at the appropriate location into BI and BABI compounds so as to increase the binding affinity of these antagonists to the Angiotensin II receptor and accordingly increase their potency. In view of the above, derivatives of the BI and BABI compounds having one or more such charges can be prepared as follows [from FIG. 4B, it can be seen that all charges (except the tyrosinate charge) including the imidazole ring lie in the same approximate plane:]

1) All distances are given relative to the center of planar imidazole ring (either of the His amino acid in Angiotensin II or of the imidazole ring of the BI/BABI compounds).

2) The placement of the charges is defined by a line drawn through the center point of the imidazole ring which bisects the $N_3$-$C_4$ bond of imidazole ring of histidine as shown in Formula I as follows:

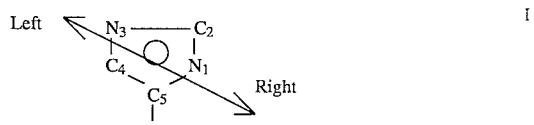

wherein the subscripts 1–5 correspond to accepted numbering of a histidine imidazole ring. [For analogs in which the His ring is rotated through 180°, e.g., His(3-methyl) analogs, the bisected bond becomes the $N_1$-$C_2$ bond.]

3. One or more of the following charges can be placed onto the imidazole ring:
   i) Direction: Left
   Charge: Cationic
   Distance from center of imidazole
   ring: 7 ±1.5 Angstroms
   (Corresponds to N-terminus cationic charge);
   ii) Direction: Right
   Charge: Anionic
   Distance from center of imidazole
   ring: 2.5 ±0.5 Angstroms
   (Corresponds to C-terminus anionic carboxylate charge);
   iii) Direction: Left
   Charge: Anionic
   Distance from center of imidazole ring: 10 ±2 Angstroms
   (Corresponds to aspartic acid anionic charge); and
   iv) Direction: Left
   Charge: Cationic
   Distance from center of imidazole ring: 12 ±2.5 Angstroms
   (Corresponds to arginine cation)

4. In the above, the orientation of the imidazole rings of Angiotensin II and the BI/BABI compounds is as shown in Formula II as follows:

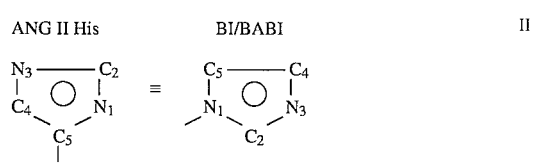

Thus $C_4$ in Angiotensin II is equivalent to $N_1$ in the BI/BABI class of compounds.

Examples of side chains which can be added to BI/BABI compounds include for instance compounds of the following Formula III:

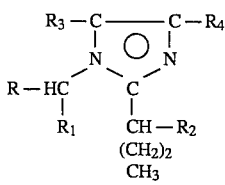

(III)

wherein R is selected from the group consisting of a) phenyl para substituted with a substituent selected from the group consisting of carboxyl or a pharmaceutically acceptable salt thereof, sulfate, and trifluoromethylsulfonamido, and b) —NHC(O)R$_5$ wherein R$_5$ is phenyl ortho substituted with a substituent selected from the group consisting of carboxyl or a pharmaceutically acceptable salt thereof, sulfate, and trifluoromethylsulfonamido, R$_1$ is either hydrogen or hereinafter defined, R$_2$ is either hydrogen or as hereinafter defined, R$_3$ is either hydroxymethyl, —CH$_2$OCH$_3$, —CH$_2$C(O)OCH$_3$, —C(O)OCH$_3$, or as hereinafter defined, and R$_4$ is either fluorine, chlorine or as hereinafter defined.

In view of the above, a compound mimicking the N-terminal cationic charge can be prepared by attaching a suitable amino group at the appropriate location on Formula III. Such a group could be placed at the appropriate distance from the center of the imidazole nucleus by employing an alkyl amino substituent (or another suitable cationic group such as a guanidino group, and the like) wherein the number of methylene groups employed in the chain linking the amino group to the BI/BABI compound is selected so as to provide a positive charge at 7 ±1.5 Angstroms left from the center of the imidazole ring. For example, placement at R$_3$ of a —(CH$_2$)$_4$—NH$_2$ group will provide such a charge (the amino group will protonate in the in vivo environment to form a —NH$_3$$^+$ group). Likewise, if hydroxyl functionality is to be maintained at R$_3$, then R$_3$ will be the group —CHOH—(CH$_2$)$_3$—NH$_2$. Alternatively, the positive charge at 7 ±1.5 Angstroms can be obtained by placement at R$_1$ of a —(CH$_2$)$_3$NH$_2$ group. In still another alternative, R$_1$ or R$_3$ can be —(CH$_2$)$_n$—Asp—Arg—NH$_2$ wherein n is 3 for R$_1$ and 4 for R$_3$ which provides for the 3 charged groups found in the N-terminal dipeptide of Angiotensin II. In regard to the above, only one of R$_1$ and R$_3$ should be substituted at any one time with a cationic group.

A C-terminal anionic mimetic can also be prepared by placing a negative charge at right 2.5 ±0.5 Angstroms to the center of the imidazole ring. For example, placement at R$_4$ of a —(CH$_2$)$_3$C(O)OH group will provide the necessary negative charge at right 2.5 ± 0.5 Angstroms (the carboxyl group will deprotonate in vivo to provide a carboxylate group, i.e., —C(O)O$^-$. Alternatively, placement at R$_2$ of a —(CH$_2$)$_3$C(O)OH will provide the necessary negative charge at right 2.5 ± 0.5 Angstroms. In regard to the above, only one of R$_2$ and R$_4$ should be substituted at any one time with an anionic group.

Similar considerations regarding the attachment of charges can be applied to the imidazole group of the His amino acid so as to arrive at mimetics to the Angiotensin II receptor. This is particularly true because as indicated above, all of the ionic charges in receptor bound Angiotensin II (except the tyrosinate anion) are in approximately the same plane and moreover, in approximately a straight line. Moreover, the imidazole ring is planar and lies in the same approximate plane as the ionic charges. Accordingly, the substituents set forth above for the imidazole group of BI/BABI compounds could be placed at their equivalent points on the imidazole of the His amino acid.

Similar groups can be designed for the aspartic acid anionic charge and for the arginine cationic charge.

The compounds depicted above can be readily prepared by the skilled artisan using art recognized techniques. Such compounds and their pharmaceutically acceptable salts are useful as Angiotensin II antagonists. Accordingly, such compounds can be used to control hypertension and/or congestive heart failure in a mammal in need of such treatment. Additionally, the compounds of this invention are contemplated as being useful in other cardiovascular and related diseases such as stroke, myocardial infarction and the like. When used to control hypertension and/or congestive heart failure, the compound is normally administered to such a mammal either orally or parenterally. When so administered, the compound is generally formulated in a pharmaceutically acceptable diluent and at a dosage sufficient to control hypertension and/or congestive heart failure in the mammal so treated. The specific dose levels for such uses can be readily determined by the skilled artisan. Accordingly, the present invention contemplates a method for controlling hypertension in a mammal in need of such treatment which comprises either administering orally or parenterally a pharmaceutical composition of a compound depicted above in an amount sufficient to control hypertension. Additionally, the present invention also contemplates a method for treating congestive heart failure in a mammal in need of such treatment which comprises either administering orally or parenterally a pharmaceutical composition of a compound depicted above in an amount sufficient to control said heart failure. The methods of controlling hypertension are implemented using pharmaceutical compositions comprising a pharmaceutically acceptable carrier and an amount of a compound depicted above effective to control hypertension in a mammal in need of such treatment. The methods of controlling congestive heart are implemented using pharmaceutical compositions comprising a pharmaceutically acceptable carrier and an amount of a compound depicted above effective to control said heart failure.

The present invention will be described in further detail with reference to the following examples. However, it should be understood that the present invention is by no means restricted by these specific examples.

EXAMPLES

A. Examples 1 and 3 below are directed to the identification by fluorescence analysis of the presence or absence of a tyrosinate charge-transfer interaction in biologically active ligands. The fluorescence analysis was measured on a nanosecond, or shorter, time intervals. Fluorescence decay due to excited-state tyrosinate emitting at and around 350 nm was determined after excitation with light of a suitable wavelength, e.g., 275 nm. The experimentally obtained fluorescence decay, which is described as a sum of exponentials, was deconvoluted, and the lifetime of the longest component due to tyrosinate was determined. In solvents of intermediate polarity, such as propylene glycol, isopropanol and the like, or in membrane environments, a lifetime in excess of about 11 nanoseconds for the long lifetime fluorescence of the excited-state tyrosinate is diagnostic of the existence of a particularly stable tyrosinate charge transfer interaction in the subject material.

Example 1

Fluorescence Properties of Angiotensin II

Angiotensin II was obtained from Sigma (acetate form) and from Peninsula Labs (trifluoroacetate form) and was found to contain a single peptide by reverse-phase HPLC. Analogs of Angiotensin II were synthesized, purified and bioassayed by method described by Matsoukas et al., J. Med. Chem., 31, pp. 1418–1421 (1988). 1,2-propanediol [Pr(OH)$_2$] was dried by refluxing over calcium oxide for 8 hours, collected by distillation and stored over a molecular sieve. Water content was estimated by $^1$H NMR or by the Karl Fisher method. Isopropanol (PrOH) was of HPLC grade (Caledon Laboratories Ltd) and was expected to contain less than 1% water. Dimethyl sulfoxide (DMSO) and trifluoroethanol (TFE) were used without further treatment. Aqueous solvents were prepared from distilled water which had been passed through Fisher ion-exchange cartridges. N-acetyl-tyrosine-amide (NAYA) was obtained from Sigma. Sodium dodecylsulfate (SDS) was obtained from BDH biochemicals (specially pure) and was used without further treatment.

Fluorescence experiments were performed at 21° C. and sample concentration of Angiotensin II used for fluorescence analysis were typically between 0.25 and 1.0 mg/mL. The samples can be warmed to about 50° C. to facilitate dissolvement of the peptide. If desired, the samples can then be filtered. Cuvettes were cleaned with sulfochromic acid and were soaked in the highly purified solvent of the experiment. Nanosecond time-resolved fluorescence decays were measured at 21° C. using Photochemical Research Associates (PRA) fluorescence lifetime instrumentation (System 3000). This instrument utilizes the time correlated single photon counting technique. A PRA 510 flash lamp was utilized as the light source and was operated at 18.6 kHz, with 5.8 kV applied across a 4 mm electrode gap under −44 kPa of H$_2$. The excitation and emission wavelengths were selected using Jobin Yvon monochromators with slits giving an 8 nm bandpass. The lamp decay profile was obtained by measuring the scattering of light by a suspension of 2.02 μm polyvinyltoluene latex spheres in glycerol/water (1:1) with the excitation and emission monochromators set at the emission wavelength of the sample. In all experiments data were collected until 2.5×10$^5$ photon counts were obtained. Background counts were obtained for each solvent and were subtracted from the sample data; the background obtained during the time of the sample collection was less than 7% of the counts at the tail end of the sample decay. The observed decay data were deconvoluted beginning from 5 channels before the channel maximum to the channel which contained the 0.05% of the photon counts present in the channel of maximum counts. The deconvolution method used was that of iterative non-linear least squares. See Grinvald et al., Anal. Biochem., 59, pp. 583–598 (1974). Acceptance of a least squares fit at 95% confidence was evaluated by the reduced chi-squared test, and the quality of fit was evaluated from the residuals, the autocorrelation function of the residuals, and the Durbin-Watson parameter. See Lampert et al., Anal. Chem., 55, pp. 68–73 (1983).

The experimentally obtained fluorescence decay, f(λ,t), is described as a sum of exponentials:

$$f(\lambda,t) = \Sigma \alpha_i(\lambda) \exp[-t/\tau_i(\lambda)] \quad (1)$$

where $\alpha_i(\lambda)$ and $\tau_i(\lambda)$ are the preexponential weighting factor and fluorescence lifetime of the $i^{th}$ component for a given emission wavelength, respectively. The fraction of the fluorescence intensity that arises from each component is related by:

$$\text{Int \%}(\lambda) = \frac{\alpha_i(\lambda)\tau_i(\lambda)}{\Sigma \alpha_i(\lambda)\tau_i(\lambda)} \times 100 \quad (2)$$

Normalized fluorescence decay curves for angiotensin II were obtained in propylene glycol, isopropanol and 0.1M aqueous SDS. Triexponential fits to the data (equations 1 and 2) gave two parameters: the lifetime of the longest fluorescence component (LLF), and the percentage of the intensity arising from the longest decay component % LLF. The observed LLF for angiotensin II in propylene glycol was 20.8 nanoseconds and the percent LLF was 19. For angiotensin II in isopropanol the LLF was 15.5 nanoseconds and the percent LLF was 79. In trifluoroethanol, angiotensin II gave LLF equals 13.0 nanoseconds and percent LLF equals 19. In aqueous SDS (SDS above the critical micelle concentration), angiotensin II gave LLF equals 13.7 nanoseconds and percent LLF equals 14.

The finding that the addition of SDS above its critical micelle concentration in water induces tyrosinate fluorescence suggests that intramolecular hydrogen bond formation of the tyrosine hydroxyl in Angiotensin II could occur in the presence of a cell membrane but not in its absence. Both the stability of the tyrosinate species (LLF) and the percent conformer providing for the tyrosinate species (% LLF conformer) were significantly increased when the SDS micelles were formed in the presence of Angiotensin II (LLF=13.7) compared to when preformed SDS micelles were added to a solution containing Angiotensin II (LLF= 7.2). The former represents a situation where Angiotensin II becomes trapped within the hydrophobic interior of the micelles, whereas the latter represents binding of the positively charged Angiotensin II to the negatively charged exterior surface of the micelle. Differences in tyrosinate fluorescence in these embodiments indicate that the tyrosinate species is stabilized even in an extremely non-polar (hydrophobic) environment, i.e., environments having a dielectric constant of about 2. Accordingly, such non-polar environments are receptor simulating environments.

Analogs of angiotensin II with agonist activities less than 1% of the agonist activity of angiotensin II in the rat uterus assay had LLF less than 11 nanoseconds in propylene glycol, and analogs with about 10% or less agonist activity had LLFs less than 12 nanoseconds in isopropanol. For example, [Sar$^1$Ile$^8$]Angiotensin II gave LLF equals 0 in propylene glycol and LLF equals 6.5 nsec in isopropanol.

Changing the concentration of the sample did not affect the parameters obtained, therefore dimerization or multiple aggregates can be ruled out as possible conformations responsible for the LLF component.

The above data demonstrates that the existence of a charge-transfer interaction involving the tyrosinate residue in a specific ligand can readily be determined by evaluating the LLF of the tyrosine moiety in the ligand.

Example 2

Structure Activity Relationship For Angiotensin II

Structure activity relationships were conducted on Angiotensin II by preparing the analogs [Sar$^1$Ala$^6$]Angiotensin II and [Sar$^1$Phe-NH$_2$]Angiotensin II. The LLFs, % LLF and Agonist Activity for these analogs are set forth in Table I above. The absence of LLFs greater than about 12 nanoseconds in these analogs implicates both the imidazole and C-terminal carboxylate of Angiotensin II in the charge-transfer interaction. Additionally, the lack of significant agonist activity in the analogs corroborates this finding.

Example 3

Fluorescence Properties and Structural Activity Properties of Oxytocin

Using the fluorescence technique described above, oxytocin had an LLF equal to 18.5 nanoseconds in propylene gylcol. On the other hand, an analog of oxytocin, [Ala$^5$], had an LLF of 7.6 nanoseconds in propylene gylcol. Accordingly, this establishes that the asparagine occupying position 5 in oxytocin is involved in the charge-transfer interaction. Additionally, this analog possessed no agonist activity, which corroborates this finding.

NMR SPECTROSCOPY

Conformational analysis of ligands is achieved by 2D COSY coupled with 1D NMR, 1D NOE enhancement or 2D NOE (ROESY) methods, using a receptor simulating solvent. If the receptor simulating solvent does not contain exchangable deuterium groups, then small amounts of $D_2O$ can optionally be added to the DMSO for exchange purposes. NOE or ROE effects observed as a result of intramolecular through-space relaxations are recorded; interresidue NOEs illustrate the proximity of neighboring groups and thereby provide valuable conformational information. This information is used to construct a molecular model of the ligand. The procedure is facilitated if the presence of a tyrosinate-forming interaction has already been established by fluorescence spectroscopy.

Example 4

2D-ROESY Proton NMR Study of [Sar[1]]Angiotensin II

[Sar[1]]Angiotensin II was synthesized by the solid phase technique and purified to homogeneity by reversed-phase HPLC using methods described by Matsoukas et al., J. Med. Chem. 31(7), pp. 1418–1421 (1988). The synthetic peptide gave the required amino acid analysis and appeared as a single product in two thin layer chromatography (TLC) systems. [Sar[1]]Angiotensin II had 180% of the bioactivity of Angiotensin II in the rat uterus assay which is also described by Matsoukas et al., supra. Since HPLC afforded the trifluoroacetate salt of the peptide, [Sar[1]]Angiotensin II was neutralized by passage through a column (1.5×3 cm) of carboxymethylcellulose (Whatman CM23) cation exchange resin. The peptide (10 mg) was first applied to the column in 0.01M ammonium acetate at pH 5 (5 ml) and then eluted with 0.5M ammonium acetate at pH 8 (10 ml). The effluent obtained at pH 8 was lyophilized thrice and 5 mg of the product was dissolved in 0.5 ml of DMSO-$d_6$ and two drops of $D_2O$ were added. Argon was bubbled through the sample for 5 minutes before the NMR tube was sealed.

NMR experiments were carried out using a Bruker AM 400 MHz NMR spectrometer, which was modified to perform spin-locking with an effective radio frequency field of 5 KHz at ambient temperature (297 ±1° K.). Data acquisition and data processing were controlled by an Aspect 3000 computer equipped with an array processor using Bruker 1987 DISNMR software. The chemical shifts were reported relative to the undeuterated fraction of the $CH_3$ group of DMSO-$d_6$ at 2.50 ppm with respect to TMS. One-dimensional spectra were recorded with a sweep width of 6100 Hz, and 32K (zero filled to 64K) data points. A total of 64 scans were accumulated to obtain a good signal-to-noise ratio. Methods used were as described by Otter et al., Biochemistry, 27(10), pp. 3560–3567, (1988), and Marion et al., Biochem. Biophys. Res. Commun., 113(3), pp. 967–974 (1983). The parameters employed in the two-dimensional NMR techniques are summarized in Table II below:

TABLE II

Summary of Experimental Parameters used in the Two-Dimensional NMR Experiments[e,f]

| Parameters | Unit | COSY | ROESY PH |
|---|---|---|---|
| Sweep Width in $F_2$ ($H_2$) | Hz | 4000 | 3300 |
| Sweep Width in $F_1$ ($H_2$) | Hz | 2000 | 1650 |
| Matrix size ($F_1$ × $F_2$) before zero filling | — | 512 × 1K | 256 × 1K |
| Matrix size ($F_1$ × $F_2$) after zero filling | — | 1K × 8K | 1K × 2K |
| Evolution time | | | |
| initial value (μs) | μs | 3 | 1 |
| increment (ms) | ms | | 78 |
| No. of scans (dummay scans) | | 32 | 64 |
| Acquistion time | s | 0.32 | 0.20 |
| Relaxation delay (HDO presaturation) | s | 1.8 | 1.8 |
| Other delays[g] | ms | | 200 |
| Window functions for 2D FT ($F_1/F_2$) | | ⅖ | ⅖ |
| Shifts of window functions in fractions of $\pi(F_1/F_2)$ | | ⅝ | ¾ |

[e] = all spectra were recorded at 297° K. at 10 mM concentration in DMSO-$d_6$ (+2 drops $D_2O$)
[f] = After the Fourier transformation, the phase, was optimized in both dimensions by an additional phase correction applied to the entire matrix. The ROESY spectrum was baseline corrected in $F^1$ and $F_2$ by means of a Bruker ABS baseline correction.
[g] = Spin locking time, at an average rf field of 5 KHz.

Both pulse sequences incorporated a decoupler presaturation interval to suppress the water signal. The resulting 2D matrices were displayed and slight phase adjustment in both dimensions were usually necessary to obtain the best possible data representation. Correlations were verified by examining individual rows and columns of unsymmetrized and symmetrized spectra.

The ROESY experiment required a basic 90° phase correction in $t_1$ before the phase fine tuning could be done. A carrier frequency of 3.7 ppm, a spin-locking time of 0.2 sec. and 30° flip angle for the hard pulse spin locking train were selected. It should be noted that this experiment often suffers from spurious resonances due to magnetization transfer between scalar coupled spins. Under the selected experimental conditions, the resulting two-dimensional spectrum was almost free of such peaks, which are otherwise easily identified by their phase being the same as the diagonal signals (real ROE cross-peaks have opposite signs with respect to the diagonal peaks). Some baseline distortions were present, especially around intense peaks such as the residual solvent signals and methyl groups. To diminish this problem, spectra were treated in both dimensions with the Bruker ABS baseline correction routine using a polynomial fitting of fifth degree to the baseline. Since all the recorded two-dimensional spectra suffer from considerable $t_1$ noise and ridges, caution was exercised to obtain reliable information from the spectra. Because only coupling connectivities were of interest, we found it useful to record the magnitude spectrum in the case of the COSY experiment; the ridges along $t_1$ can then be reduced considerably by methods described by Otter et al., supra.

All resonances of the peptide were assigned to individual amino acids by combined information from COSY and ROESY spectra as set forth in Example 5 below. Our assignments for [Sar[1]]Angiotensin II differ from those reported previously for Angiotensin II [by Smeby et al., Chemistry and Biochemistry of Amino Acids, Peptides and Proteins, Ed. Weinstein, Dekker, N.Y., pp. 117–162 (1976)] only with regard to the relative positioning of the Phe $C_\alpha$ proton within the $C_\alpha$ group. Symmetrized and unsymmetrized ROESY spectra were examined to identify both intraresidue and interresidue cross-peaks. Table III below shows all ROESY interactions, both intraresidue and interresidue:

TABLE III

Proton:proton ROESY interactions identified for [Sar$^1$]Angiotensin II in DMSO-d$_6$ + D$_2$O$^{h,i,j,k,l}$

| Sar | Arg (R) | Val (V) | Tyr (Y) | Ile (I) | His (H) | Pro (P) | Phe (F) |
|---|---|---|---|---|---|---|---|
| | | | Intraresidue interactions | | | | |
| α:M | α:β | α:β | α:β | α:β | β:β' | α:β | α:β |
| | α:β' | β:γ | α:β' | β:γ | α:C$_4$ | α:β' | β:β' |
| | β:γ | α:γ | β:β' | β:γ | | β:γ | α:F$_Φ$ |
| | γ:δ | | α:m | γ:δ | | γ:δ | β:F$_Φ$ |
| | α:γ | | β:m | α:γ | | γ:δ' | β':F$_Φ$ |
| | α:δ | | β':m | α:γ' | | δ:δ' | |
| | β:δ | | m:o | γ:γ' | | | |
| | | | | α:M | | | |
| | | | | β:M | | | |
| | | | Interresidue interactions | | | | |
| M:Y$_o$ | | V$_M$:Y$_m$ | Y$_m$:V$_M$ | H$_α$:P$_δ$ | P$_δ$:H$_α$ | F$_Φ$:Y$_o$ | |
| | | | Y$_o$:F$_Φ$ | H$_α$:P$_δ'$ | P$_δ$:H$_α$ | F$_Φ$:P$_γ$ | |
| | | | Y$_o$:Sar$_M$ | | | P$_γ$:F$_Φ$ | |

$^h$ = M stands for methyl group protons.
$^i$ = Meta (m) and ortho (o) refer to the hydroxyl group on tyrosine.
$^j$ = The signals for phenylalanine ring protons (Φ) overlap and were not individually assigned.
$^k$ = β', γ', and δ' refer to the upfield geminal proton resonance.
$^l$ = The amino acid abbreviations used below are the conventional art recognized abbreviations.

Interresidue interactions are extremely important for studying the conformation of [Sar$^1$]Angiotensin II in DMSO. Thus the cross-peaks for the Tyr ortho:Phe ring protons, together with the cross-peaks for Pro C$_γ$:Phe ring protons and Pro C$_δ$:His C$_α$ protons, illustrate the proximity of Tyr with both His and Phe and suggest that the three aromatic rings in Angiotensin II are in close proximity.

Useful information concerning the rotational freedom of the three aromatic side chains was obtained by examining the intraresidue ROE connectivities between $C_α$ and $C_β$ protons. For Tyr the interaction of the $C_α$ proton with the $C_β$ proton (δ=2.80 ppm) was much stronger than the interaction of the $C_α$ proton with the $C_{β'}$ proton (δ=2.62 ppm), indicating hindered rotation of the Tyr side chain. For Phe only the $C_{β'}$ proton (i.e., the proton at δ=2.85 ppm) interacts with the $C_α$ proton (δ=4.10) again indicating the presence of a preferred rotameter and possibly less motion for the Phe side-chain than the Tyr side-chain. For His neither of the $C_β$ protons (δ$_1$=2.86 ppm and δ$_2$=2.75 ppm) appeared to interact with the $C_α$ proton (δ=4.60 ppm). By examining rows and columns only a very weak interaction could be observed between His $C_α$ and $C_β$ protons; this suggests that the $C_α$–$C_β$ bond of His may be essentially fixed in the trans form in DMSO.

The interaction of the His $C_α$ proton with both Pro $C_δ$ protons not only illustrates that the His$^6$-Pro$^7$ bond exists primarily in the trans form, but also defines the orientation of the His-Pro bond. A further connectivity present in the ROESY spectrum involves a strong interaction between a methyl group of Val or Ile with the $C_α$ proton of Ile, Val or Phe. Definitive assignment of these cross-peaks could not be made because of signal overlap, but probably represent an intraresidue interaction of Ile and/or Val. Similarly, an interresidue interaction between Tyr meta and a methyl group of Ile or Val could not definitely be assigned. A weak connectivity was also observed between the Sar NCH$_3$ proton (δ=2.23 ppm) and a Tyr ortho proton (δ=6.58 ppm). A connectivity between the Tyr ortho and His C$_4$ ring protons was observed in rows but not in columns.

For Arg, the $C_α$ proton (δ=4.32 ppm) appeared to interact with all side-chain methylene protons. Thus, connectivities were observed between the $C_α$ proton and 1) the two $C_β$ protons (1.65 and 1.35 ppm), 2) the two $C_γ$ protons (1.48 and 1.42 ppm), and 3) a $C_δ$ proton at 3.02 ppm (another connectivity between the Arg $C_α$ proton and a proton at 3.45 ppm was tentatively assigned to a Arg $C_δ$ proton). Non-equivalence of the three geminal proton pairs may indicate restricted rotation for the Arg side-chain. ROEs between $C_α$ and $C_δ$ protons may illustrate folding of the Arg side-chain.

Interactions between the Tyr ortho:Phe ring protons, together with connectivities between the Phe ring:Pro$_γ$C protons and His $C_α$:Pro $C_δ$ protons, suggest that all three aromatic rings in Angiotensin II are in close proximity and form a cluster in DMSO. No ROE cross-peaks were observed between the His and Phe residues. A previous report describing shielding of the His ring by the Phe ring in DMSO [see Matsoukas et al., Biochem. Biophys. Res. Commun., 122(1), pp. 434–438 (1984)] may reflect indirect effects, resulting from clustering of the three rings. Alternatively, the His and Phe rings may be separated by a distance which allows for an electrostatic interaction but is beyond the maximum range (<5 Angstroms) for an observable ROE. Similar considerations may explain the absence of an observable two-way ROE between the Tyr and His rings.

The relative orientation of the rings to one another in the cluster cannot be deduced without further information. However, some helpful information is supplied in the form of connectivities between non-aromatic protons, as illustrated in Table III. In particular, the observation of through space interactions between the His $C_α$ and the two Pro $C_δ$ protons defines the orientation of the His-Pro backbone and demonstrates the predominace of the trans isomer in DMSO. It can be deduced that the C-terminal Phe residue must swing around through about 90° in order that the Phe ring can interact with the central Tyr ring (Table III). Modelling experiments illustrate that the Phe residue is most likely to approach the Tyr-Ile-His sequence from a γ turn originating at the His-Pro bond.

The ROESY spectrum shows strong intraresidue $C_β/C_{β'}$ interactions in all three aromatic residues (Tyr, His, and Phe), illustrating non-equivalence and restricted rotation for these geminal protons. Moreover, non-equivalent interresidue interactions between the $C_α$ proton and the two $C_β$ protons were observed for Tyr, only one $C_α/C_β$ intraresidue interaction was observed for Phe, and $C_α/C_β$ interactions for His were very weak. These finding suggest that the $C_α$–$C_β$ bonds of all three aromatic side-chains are unable to freely rotate. For His the $C_α$–$C_β$ bond protons appear to be locked in the trans position, whereas for Tyr and Phe the $C_α$–$C_β$ bond protons may be fixed (on the NMR time scale) between the gauche and trans orientatins. Restricted rotation for the Phe ring may originate from interaction with the His side chain, the C-terminal carboxylate and/or an interaction with the Pro ring. The latter interaction is evidenced in the ROESY spectrum by cross-peak connectivities between Phe ring and Pro $C_γ$ and $C_{γ'}$ protons. These interresidue interactions were non-equivalent; the interaction of the Phe ring proton(s) with the lower field Pro $C_γ$ proton at δ=1.70 ppm, appeared to be considerably stronger than the interaction with the upfield Pro $C_γ$ proton at δ=1.50 ppm. This indicates that the Phe and Pro rings are close but that the Phe ring probably approaches the Pro ring in a non-parallel manner. These findings are in agreement with previous proposals which have suggested functional roles for the three aromatic side-chains, and steric/spatial roles for Ile and Val. See Moore, Pharmacol. Ther., 33(2–3), pp. 349–381 (1987). More specifically, it has been suggested that motion of the His and Phe side-chains would be inhibited by interaction with the C-terminal carboxylate and each other, whereas the Tyr side-chain would be constrained by H-bonding with His. Such considerations could explain why the $C_\alpha$–$C_\beta$ bond of His exists predominantly in the energetically less favorable eclipsed conformation, since the energy gained from the charge-transfer interaction could overcome the energy loss due to an eclipsed His $C_\alpha$–$C_\beta$ rotomer.

According to the overall structural features suggested by the present ROESY experiment, certain previously proposed interactions [see Moore et al., Biosci. Rep., 5(5), pp. 407–416, (1985)] are permissable. Thus, modelling experiments illustrate that the Tyr hydroxyl could hydrogen bond to an imidazole ring nitrogen of the His residue and that the C-terminal carboxylate could also interact with the His ring. These interactions appear to be possible in DMSO without introducing undue constraint in the molecule. Proximity of the C-terminal carboxylate to one of the His ring nitrogens would serve to increase the polarization of the His ring dipole, thereby increasing the basicity of the other His ring nitrogen and the strength of its interaction with the Tyr OH. This interaction may result in the production of a tyrosinate species which activates the receptor.

The present investigations have shown an interresidue interaction of the $Sar^1$ residue with the $Tyr^4$ ring. [$Sar^1$] Angiotensin was selected in part for this study so that information on interactions of the N-terminal could be readily observed. In this regard, 1D NMR spectra conducted for Angiotensin II and [$Sar^1$]Angiotensin II in DMSO have shown that the aromatic region of these spectra are identical. The importance of the $Sar^1$ residue in contributing to the antagonist activity in Sarmesin is well documented and previous studies have shown that the N-$CH_3$ of $Sar^1$ is subjected to a shielding influence in a number of angiotensin analogues in DMSO. See Moore et al., Biosci. Rep., 5(5), pp. 407–416, (1985). The results of this ROESY example support previous suggestions [Matsoukas et al., Peptides 1986, Ed. Theodoropoulos et al., Berlin, N.Y., pp. 335–339 (1987)] that the Sar $NCH_3$ interacts with the Tyr ring. In particular, examination of the rows and columns containing the Sar $NCH_3$ of the symmetrized and unsymmetrized ROESY spectrum indicated a weak connectivity with a Tyr ortho proton. Thus the source of the shielding effect on the $NCH_3$ could be the Tyr ring, and the Sar $NCH_3$ group may exist just at the limiting range for observing an ROE.

Summarizing the above ROESY results, cross-peaks between aromatic rings provided evidence that the three aromatic rings of [$Sar^1$]Angiotensin II cluster together. Cross-peaks between the His $C_\alpha$ proton with both Pro $C_\delta$ protons illustrated that the $His^6$-$Pro^7$ bond exists primarily in the trans form. Cross-peaks between the Sar $NCH_3$ proton and a Pro ortho proton illustrated proximity of the N-terminus of the peptide with the Tyr ring. An observed cross-peak between the Phe ring protons and the Pro $C_\gamma$ protons illustrated that the Phe ring is close to the Pro ring [as well as the His ring, previously noted].

The information obtained from the 2-D ROESY experiment together with the fluorescence data showing the presence of a tyrosinate charge transfer system, enables the construction of a molecular model for [$Sar^1$] angiotensin II. This model is shown in FIG. 1.

Likewise, by following the procedures set forth above and because similar cross-peaks have been observed for angiotensin II, a molecular model of Angiotensin II has been constructed and is set forth in FIG. 4A. Stereo photographs of this model are illustrated in FIGS. 6 and 7.

The model for Angiotensin II shown in FIG. 4A differs from previously reported conformations. In particular, the N-terminus and the Phe ring have been repositioned in FIG. 4 in order to accomodate the presently observed proximity of the Tyr ring with both the N-terminus and the Phe ring. Repositioning of the Phe ring is also compatible with ab initio calculations of ring pairing interactions which have suggested a perpendicular-plate interaction for the His and Phe rings. Fowler et al., Biochem. Biophys. Res. Commun., 153(3), pp. 1296–1300 (1988).

Example 5

1D-NOE Enhancement For Samesin

Sarmesin and [$Des^1$]Sarmesin were synthesized by in a similar solid phase technique described in Example 4 above. Purification by reversed-phase HPLC afforded the trifluoroacetate salt of the peptides which were neutralized by passage through a carboxymethylcellulose column as described as well in Example 4 above.

NMR experiments were carried out using a Bruker 400 MHz NMR spectrometer. 5 mg of peptide was dissolved in 0.5 ml of DMSO-$d_6$ and two drops of $D_2O$ were added. Argon was bubbled through the sample for 5 min. before the NMR tube was sealed. Data acquisition and data processing were controlled by an Aspect 3000 computer equipped with an array processor using 1987 DISNMR software. The chemical shifts were reported relative to the undeuterated fraction of the methyl group of DMSO-$d_6$ at 2.50 ppm with respect to TMS. One-dimensional spectra were recorded with a sweep width of 4500 Hz, and 32K (zero filled to 64K) data points. A total of 64 scans were accumulated to obtain a good signal-to-noise ratio. The methods used were similar to those reported by Otter et al., J. Am. Chem. Soc., 109, pp. 6995–7001 (1987). The COSY (two-dimensional correlated spectroscopy) experiments provided contour plots which were symmetrized with respect to the diagonal. The nonselective longitudinal $^1H$ relaxation times were determined in DMSO-$d_6$+$D_2O$ (2 drops) using a 180°-τ-90° plus sequence and are presented in Table IV below.

TABLE IV

| Proton $T_1$ Relaxation Times (in seconds) for Sarmesin | | | | |
|---|---|---|---|---|
| A. Aromatic Side Chains | | | | |
| His | | Tyr(Me) | | |
| $C_2H$ 0.332 | | meta | 1.180 | |
| $C_4H$ 0.481 | | ortho | 1.505 | |
| | | $CH_3$ | 0.994 | |
| B. Backbone protons | | | | |
| His | Tyr(Me) | Ile | Val | Phe(Arg,Pro) |
| $H_\alpha$ 0.436 | $H_\alpha$ 0.962 | $H_\alpha$ 0.726 | $H_\alpha$ 0.853 | $H_\alpha$ 0.896 |
| C. Other | | | | |
| | | Sar | | |
| $H_\alpha$ 0.559 | | | $CH_3$ 0.805 | |

Several τ values ranging between 0.01 and 10 s were employed. Relaxation delays of up to 10 s were used for $T_1$ measurements.

One-dimensional NOE enhancement measurements were carried out in the difference mode using multiple irradiation. Each of the selected lines was irradiated 50 times for 100 ms (total irradiation time 5.0 s). Other irradiation times (0.2, 0.5, 1 and 3 s) were also employed in some experiments to monitor the NOE build-up. The multiple irradiation procedure allows a very low decoupler power setting (typically 10 dB lower than for a standard NOE experiment) so that it is possible to avoid partial saturation of resonances in close proximity. A total of 1000 scans for each line was required, and total relaxation time was 2 s. Under the experimental conditions used for the NOE experiments (low power, different τ preirradiation times, saturation of control areas), spin diffusion and partial saturation were visibly minimized for the interactions under discussion. NOE enhancements were determined as the point increase in signal size per proton after saturation of a functionally distinct proton. Table V below sets forth the resulting NOE enhancements:

TABLE V

NOE enhancements for Sarmesin and [Des$^1$]Sarmesin$^m$

| Peptide | Proton(s) sat. | Enhancement | % proton | Rat. |
|---|---|---|---|---|
| A | Tyr(Me) $C_\alpha$ | Tyr(Me) $C_{\beta\beta'}$ | 8.7 | C |
| A | Phe $C_\alpha$ [+Val, Ile] | Phe $C_{\beta\beta'}$ | 2.4 | C |
| A | His $C_\alpha$ | His $C_{\beta\beta'}$ | 8.2 | C |
| A | His $C_\alpha$ | Pro $C_\delta$ | 11.3 | D |
| A | His $C_\alpha$ | Pro $C_{\delta'}$ | 8.6 | D |
| A | Arg $C_\alpha$ | Arg $C_{\beta\beta'}$ | 2.5 | C |
| A | Arg $C_\alpha$ | Arg $C_{\gamma\gamma'}$ | 1.5 | C |
| A | Arg $C_\alpha$ | Arg $C_{\delta\delta'}$ | 1.1 | C |
| A | Sar $C_\alpha$ +Pro $C_\delta$] | Sar $CH_3$ | 1.2 | C |
| A | Sar $CH_3$ | Sar $C_\alpha$ | 0.9 | C |
| A | Sar $CH_3$ | His $C_\beta$ | 1.1 | D |
| A | Pro $C_\delta$ [+Sar $C_\alpha$] | His $C_\alpha$ | 5.0 | D |
| A | Pro $C_\delta$ [+Sar $C_\alpha$] | Pro $C_{\delta'}$ | 9.0 | C |
| B | Tyr(Me) $CH_3$ | His $C_2$ | 0.4 | D |
| B | Tyr(Me) $CH_3$ | His $C_4$ | 0.5 | D |
| B | Tyr(Me) $CH_3$ | Tyr(Me) ortho | 6.7 | C |
| B | Tyr(Me) $CH_3$ | Tyr(Me) meta | 3.2 | E |
| B | Tyr(Me) meta [+Phe] | Tyr(Me) ortho | 18 | C |
| B | His $C_2$ | Tyr(Me) meta | 2.1 | D |
| B | His $C_2$ | Tyr(Me) ortho | 1.6 | D |

$^m$ = in DMSO-$d_6$
A = Sarmesin
B = [Des$^1$]Sarmesin
C = intraresidue NOE
D = interresidue NOE
E = spin diffusion Sarmesin and [Des$^1$] Sarmesin were subjected to two-dimensional correlated spectroscopy (COSY) and nuclear Overhauser enhancement (NOE) experiments, suitable for resonance assignment and distance information. It was possible to assign peptide resonances to individual amino acids by combining information from the COSY and NOE difference spectra. The one-dimensional NMR spectra of Sarmesin and [Des$^1$]Sarmesin in DMSO-$d_6$ showed a complex downfield region with broad overlapping NH resonances indicating fast exchange. To simplify the $C_\alpha$ proton and aromatic regions and to study the intramolecular proton-proton interactions between aromatic rings and interresidue backbone protons, the NMR experiments were carried out after the NH's were exchanged with $D_2O$.

The NOE experiments combined with the COSY spectrum permit complete assignment of all backbone and side-chain proton resonances. Saturation of the $C_\alpha$ protons of His, Tyr(Me), and Phe (overlapped with the $C_\alpha$ protons of Val and Ile), resulted in an enhancement of the vicinal β protons revealing their pattern and exact position in the crowded aliphatic region of the reference spectrum. Thus, the NOE difference spectrum which resulted after saturation of the His $C_\alpha$ proton at δ=4.64 ppm, showed an AB quartet at δ=2.86 ppm attributable to the two vicinal His $C_\beta$ protons. This interaction was measured to be 8.2%. Similarly, the NOE difference spectra which resulted after saturation of the Tyr(Me) $C_\alpha$ proton at δ=4.48 ppm and the Phe $C_\alpha$ at δ=4.11 ppm, show an AB quartet for the vicinal Tyr(Me) and Phe $C_\beta$ protons at δ=2.77 ppm (8.7%) and 2.95 ppm (2.4%).

The NOE difference spectrum resulting after saturation of the His $C_\alpha$ proton also shows two strong resonances at δ=3.20 ppm (11.3%) and 3.49 ppm (8.6%) due to enhancement of the two Pro $C_\delta$ protons. Both Pro $C_\delta$ protons are almost equally affected, revealing close proximity and equidistance of both of these protons from the His $C_\alpha$ proton. This interaction, which also has been observed for [Sar$^1$] Angiotensin II in DMSO (Example 4 above), confirms the presence of the trans form of the His$^6$-Pro$^7$ bond and permits insight into the relative orientation of the His-Pro-Phe sequence. The stereochemistry around the His-Pro bond in Angiotensin II has been the subject of many investigations using mostly $^1$H and $^{13}$C-NMR spectroscopy. The results of this example using proton:proton NOE enhancement confirm these findings and, furthermore, define the precise orientation of the His-Pro bond.

Saturation of the $C_\alpha$ proton of the Arg and Pro at δ=4.34 ppm and at δ=4.21 ppm, respectively, revealed multiplet patterns for the respective vicinal β protons at δ=1.58 ppm and δ=1.75 ppm in the NOE difference spectra. A resonance enhancement observed at δ=3.02 ppm (1.6%) upon saturation of the Arg $C_\alpha$ proton was tentatively attributed to an interaction with the Arg $C_\delta$ protons. This interaction, observed also in [Sar$^1$]Angiotensin II during rotating frame nuclear Overhauser effect spectroscopy studies (Example 4), illustrates proximity of the Arg $C_\alpha$ protons with the Arg $C_\delta$ protons. Saturation of the Sar $C_\alpha$ protons resonance at δ=3.2 ppm resulted as expected in the enchancement of the Sar $CH_3$ proton resonance at δ=2.26 ppm (1.2%). Conversely, irradiation of Sar $CH_3$ enhanced the Sar $C_\alpha$ protons (0.9%). In addition, enhancement of one of the His $C_\beta$ protons was observed after Sar $NCH_3$ saturation, implying proximity of the Sar $CH_3$ protons to one of the His $C_\beta$ protons. The observed enhancement of the His $C_\alpha$ proton resonance at δ=4.64 ppm (5%) and the downfield Pro $C_\delta$ proton resonance at δ=3.48 ppm (9%) can be attributed to the saturation of the upfield Pro $C_\delta$ proton resonance which is overlapped with the Sar $C_\alpha$ proton resonance at δ=3.20 ppm.

To investigate the proposed proximity of the Tyr and His rings, [Sar$^1$]Angiotensin II and [Des$^1$]Angiotensin II (Angiotensin III) were methylated at the Tyr hydroxyl so as to provide a suitable probe (δ–3.61 ppm) for investigating interaction between the two aromatic rings. For these reasons, NOE experiments were carried out by saturating the Tyr $OCH_3$ resonance and the His $C_2$ and $C_4$ proton resonances in both analogs. Upon saturation of the Tyr $OCH_3$ resonance of [Des$^1$]Sarmesin ([Tyr(Me)$^4$]Angiotensin III), weak enhancements of the His $C_2$ and $C_4$ proton resonances at δ=7.47 ppm (0.42%) and δ=6.85 ppm (0.52%), respectively, were observed. The weakness of these interactions places the Tyr $OCH_3$ group at the limit of the permissable distance (<5 Angstroms) from the His imidazole ring for the effect to be observed. The cancellation of the Phe ring resonance at the vicinity of the Tyr meta resonance suggests that the observed effect may be real and not due to spin diffusion. However, enhancement of the Tyr ortho and meta proton resonances at δ=7.82 ppm (3.21%) and δ=6.71 ppm (8.86%) was observed upon saturation of the Tyr $OCH_3$ protons in [Des¹]Sarmesin. Whereas the former is an expected Overhauser effect, the latter may result from second-order magnetization transfer via the ortho protons. The possibility cannot be ruled out that the enhancements of His $C_2$ and $C_4$ in [Des¹]Sarmesin result from secondary NOEs relayed by Tyr ortho and/or meta protons, although such considerations would still place the Tyr and His rings in close proximity. Since similar NOE enhancements of the His $C_2$ and $C_4$ protons were not observed for Sarmesin, the presence of the N-terminal Sar may subtlely alter the conformation of the octapeptide and place the Tyr $OCH_3$ group just outside the boundary for permissible and observable NOE interactions with the His ring.

Saturation of the His $C_2$ proton resonance at $\delta=7.47$ ppm in [Des¹]Sarmesin, resulted in enhancement of the Tyr meta and ortho proton resonances at $\delta=7.08$ ppm (2.15%) and $\delta=6.71$ ppm (1.58%). However, upon saturation of the Tyr meta proton resonance at $\delta=7.09$ ppm (overlapped with the Phe ring proton resonances), no enhancement was observed for the His $C_2$ and $C_4$ protons at $\delta=7.47$ ppm and $\delta=6.85$ ppm. Only the Tyr ortho proton at $\delta=6.71$ ppm (18%) in the aromatic region under scrunity was enchanced. The latter saturation serves as a control experiment to show the minimum contribution of partial saturation to the enhancement of the Tyr meta and ortho proton signals.

The NOE difference spectra for Sarmesin upon saturation of the His $C_\alpha$, Tyr(Me) $C_\alpha$ and Phe (Val, Pro) $C_\alpha$ protons reveals intraresidue $C_\alpha/C_\beta$ proton interactions in His, Tyr(Me), and Phe. The presence of an interresidue His $C_\alpha/Pro\ C_\delta$ proton:proton NOE defines a predominantly trans conformation for the His-Pro peptide bond of Sarmesin in DMSO. The trans isomer also predominates in [Sar¹]Angiotensin II (Example 4), illustrating that both agonist and antagonist maintain this conformational property in DMSO. Furthermore, the similar effects of saturation of the His $C_\alpha$ proton on both Pro $C_\delta$ protons locates the His $C_\alpha$ proton midway between the two Pro $C_\delta$ protons.

An interresidue proton:proton NOE was observed between the Arg $C_\alpha$ Arg $C_\delta$ protons after saturation of the former in Sarmesin. This could illustrate that the Arg side-chain does not exhibit complete freedom of motion in DMSO, or that it exhibits sufficient conformational freedom to sample many conformations. The role of this positively charged side-chain may be to contact a complementary anionic site on the receptor and assist in bringing about productive binding of Angiotensin II to its receptor. The same interaction has been observed in [Sar¹]Angiotensin II (Example 4). This, together with considerations for the His-Pro bond in [Sar¹]Angiotensin II and Sarmesin, illustrates similarities in certain aspects of the conformations of the agonist and the antagonist in DMSO.

Proximity of the Sar $CH_3$ protons with one of the His $C_\beta$ protons in Sarmesin is evidenced by signal enhancement of the latter with saturation of the former. This suggests the presence of a bend in the N-terminal Sar-Arg-Val region of the molecule which allows proximity of Sar and His. Modelling experiments suggest that, for steric reasons, the N- and C-termini of the molecules probably approach the central domain from different sides, thereby creating an approximately S-shaped peptide backbone.

The NOE difference spectrum for [Des¹]Sarmesin upon saturation of the Tyr(Me) methyl protons illustrates enhancement of the His $C_2$ and $C_4$ protons. Proximity of the Tyr(Me) methyl group and the His ring is in accord with the previously postulated hydrogen bonding interaction between the Tyr OH and the His ring in Angiotensin II. Spin diffusion not withstanding, the similar NOE enhancements of both the His $C_2$ and $C_4$ protons suggests that the Tyr(Me) ring may have a perpendicular orientation relative to the imidazole ring; this deduction is based on the expected planarity of the methoxy group with the Tyr ring. This is a potentially interesting observation since the relative orientations of the Tyr and His rings may be similarly maintained in the cluster of aromatic rings in Angiotensin II. Even if enhancement of the His $C_2$ and $C_4$ resonances is due to secondary NOEs relayed by the Tyr ortho and/or meta protons, the data still establish the important fact that the Tyr and His rings are in close proximity.

Upon saturation of the His $C_2$ proton in [Des¹]Sarmesin, NOE enhancement of the Tyr(Me) meta and ortho protons is observed. Due to overlap of the His $C_4$ and Tyr(Me) meta and ortho proton signals in the NMR spectrum, it was not possible to saturate the His $C_4$ proton and obtain meaningful results. Indeed, the validity of the His $C_2$ saturation experiment is questionable and a control experiment was carried out to test the extent of partial saturation. Saturation of the Tyr(Me) meta protons resonance at $\delta=7.09$ ppm (overlapped with the Phe ring protons resonance) resulted in enhancement of the Tyr(Me) ortho protons at $\delta=6.72$ ppm (30%) but not of the His $C_2$ and $C_4$ protons resonances. This experiment favors the absence of partial saturation effects contributing to the enhancement of the Tyr(Me) meta and ortho protons resonances after saturation of the His $C_2$ proton, validating the experimental data showing proximity of the Tyr(Me) and His rings of [Des¹]Sarmesin in DMSO. Moreover, the interaction between the Tyr(Me) and His rings in [Des¹]Sarmesin is not a reverse relaxation phenomenon. Thus, while the His $C_2$ and $C_4$ protons can relax through the closely spaced Tyr(Me) meta and ortho ring protons, the reverse effect is not observed upon saturation of the Tyr(Me) meta and ortho protons. The probable reason for this is that Tyr(Me) ortho and meta protons have relaxation pathways which are not available to the His $C_2$ and $C_4$ protons. The Tyr(Me) ortho protons can relax through the Tyr(Me) meta and methyl protons, while the Tyr(Me) meta protons can relax through the Tyr(Me) ortho and $C_\beta$ protons.

In conclusion, the findings of this example suggest that Sarmesin and [Des¹]Sarmesin contain the same bend at the His-Pro bond which has been observed for [Sar¹]Angiotensin II and that this produces similar clustering of the aromatic rings. Sarmesin and Angiotensin II appear to assume an approximately S-shaped conformation in DMSO. Previous work has suggested that the N-terminus of [Sar¹] Angiotensin II interacts with the Tyr ring, whereas the present findings indicates that the N-terminus of Sarmesin is close to the His side-chain. From molecular modelling experiments, it can be shown that the Sar $NCH_3$ group can occupy a position which is close to both the Tyr ring and the His $C_\beta$ protons simultaneously.

Example 6

NMR Studies on Oxytocin and [Arg⁸] Vasopressin

NMR studies were carried out using a Bruker 400 Mz instrument essentially as described in previous examples. Peptides were dissolved at a concentration of 5 mg/0.5 ml of DMSO-$d_6$ and 2 drops of $D_2O$ were added.

A characteristic resonance for the tyrosine hydroxyl proton at $\delta=9.2$ ppm was present in the proton NMR spectrum for vasopressin, but not in the NMR spectrum for oxytocin. The absence of this signal in oxytocin is diagnostic for tyrosinate formation and agrees with the fluorescence spectroscopy (Example 3); this signal was also absent for angiotensin II.

A ring pairing interaction for vasopressin is also evident when the NMR data for the Tyr and Phe rings of vasopressin are investigated. Theoretical calculations [Fowler et al., Biochem. Biophys. Res. Commun., 153(3), pp. 1296–1300 (1988)] have illustrated that electrostatic ring pairing interactions will occur preferentially in the perpendicular-plate orientation, and that a slipped parallel-plate configuration will only be adopted when other prevailing factors override perpendicular-plate interactions. In NMR experiments, perpendicular-plate interaction is accompanied by shielding of the protons of one ring and the absence of a shielding effect on the other ring, with both rings demonstrating non-equivalence of their ring protons. This is seen for vasopressin where the Tyr ring protons in the peptide are shielded (6.91 and 6.62 ppm) compared to the protons of free Tyr (7.07 and 6.70 ppm) or the Tyr ring protons of oxytocin (7.12 and 6.68 ppm). The Phe ring protons of vasopressin are not shielded and are non-equivalent (7.34 and 7.24 ppm) compared to free Phe (7.30 ppm). This discloses the fact that the hexagonal axis of the Tyr ring interacts with the hexagonal face of the Phe ring in vasopressin. The method can be used for any molecule where a ring pairing interaction is possible.

What is claimed is:

1. A method for creating a three-dimensional spatial model for a biologically active ligand which is complementary to a membrane bound receptor wherein said ligand has at least one active site based on a charge-transfer interaction involving a phenolate species and further has a known structural formula wherein the three-dimensional spatial assignments for each of the atoms of the ligand in the model are assigned from the steps comprising:

a) determining the presence of at least one charge-transfer interaction in said ligand involving a phenolate species from fluorescence analysis of said ligand in a fluorescence compatible environment wherein said fluorescence compatible environment is a selected from the group consisting of micelies, lipid bilayers, and solvents having a dielectric constant of about 40 or less;

b) determining each chemical group involved in each charge-transfer interaction; and c) resolving remaining aspects of the ligand's three-dimensional conformation by obtaining conformational information relative to each active site from nuclear magnetic resonance spectroscopy comprising the steps of:

preparing a neutralized form of a biologically active ligand which neutralized form comprises the acetate salt wherein the biologically active ligand is the cation and the anion is an acetate anion;

providing said neutralized biologically active ligand in a receptor simulating environment which simulates a membrane bound receptor wherein said receptor simulating environment is a solvent having a dielectric constant of about 50 or less; and conducting nuclear magnetic resonance spectroscopy comprising a first step of conducting correlated spectroscopy so as to determine through-bond coupling patterns within the ligand, followed by nuclear magnetic resonance spectroscopy using the nuclear Overhauser effect on the neutralized biologically active ligand to obtain data which is a measure of the three-dimensional conformation of the biologically active ligand.

2. A method according to claim 1 wherein said biologically active ligand is selected from the group consisting of Angiotensin II, oxytocin, and vasopressin.

3. A method according to claim 1 wherein said charge-transfer interaction is a tyrosinate charge-transfer interaction.

4. A method according to claim 3 wherein said ligand has one active site based on a tyrosinate charge-transfer interaction.

5. A method according to claim 4 wherein said ligand is Angiotensin II.

6. A method according to claim 5 wherein the nuclear Overhauser effect technique comprises ROESY.

7. A method according to claim 1 wherein said nuclear Overhauser effect comprises NOESY with the proviso that the molecular weight of the ligand is less than 500 or greater than 2000 daltons.

8. A method according to claim 1 wherein the solvent comprising a receptor simulating environment is dimethylsulfoxide.

9. A method according to claim 1, wherein the solvent comprising a receptor simulating environment is selected from the group consisting of dimethylsulfoxide, trifluoroethanol, isopropanol, or propylene glycol.

10. A method according to claim 1, 8 or 9 wherein the solvent comprises a deuterated solvent.

11. A method according to claim 1 wherein the neutralized form of the biologically active ligand is prepared on an ion exchange resin to produce the acetate salt of the biologically active ligand.

12. A method for determining a conformation of a biologically active ligand which is complementary to membrane bound receptor which method comprises the steps of:

preparing a neutralized form of a biologically active ligand which neutralized form comprises a salt wherein the biologically active ligand is the cation and the anion is an acetate anion;

providing said neutralized biologically active ligand in a receptor simulating environment which simulates a membrane bound receptor environment wherein said receptor simulating environment is a solvent having a dielectric constant of about 50 or less; and conducting nuclear magnetic resonance spectroscopy comprising a first step of conducting correlated spectroscopy so as to determine through-bond coupling patterns within the ligand, followed by nuclear magnetic resonance spectroscopy using the nuclear Overhauser effect on the neutralized biologically active ligand to obtain data which is a measure of the three-dimensional conformation of the biologically active ligand.

13. A method according to claim 12 wherein the neutralized form of the biologically active ligand is prepared on an ion exchange resin to produce an acetate salt of the biologically active ligand.

14. A method according to claim 12, wherein the solvent comprises dimethylsulfoxide, trifluoroethanol, isopropanol, or propylene glycol.

15. A method according to claim 14, wherein the solvent comprises dimethylsulfoxide.

16. A method according to claim 12, 14 or 15 wherein the solvent comprises a deuterated solvent.

17. A method according to claim 12 wherein said biologically active ligand comprises a naturally occurring biologically active ligand complementary for said receptor.

18. A method according to claim 17 wherein said naturally occurring biologically active ligand is selected from the group consisting of Angiotensin II, oxytocin and vasopressin.

19. A method according to claim 12 wherein said biologically active ligand has only one charge-transfer interaction.

20. A method according to claim 12 wherein said nuclear Overhauser effect comprises ROESY.

* * * * *